(12) United States Patent
Zhang

(10) Patent No.: US 11,478,145 B2
(45) Date of Patent: Oct. 25, 2022

(54) MULTISPECTRAL AND HYPERSPECTRAL MEIBOGRAPHY

(71) Applicant: Aizhong Zhang, Rochester, NY (US)

(72) Inventor: Aizhong Zhang, Rochester, NY (US)

( * ) Notice: Subject to any disclaimer, the term of this patent is extended or adjusted under 35 U.S.C. 154(b) by 441 days.

(21) Appl. No.: 16/413,346

(22) Filed: May 15, 2019

(65) Prior Publication Data

US 2020/0359890 A1    Nov. 19, 2020

(51) Int. Cl.
| | |
|---|---|
| A61B 3/12 | (2006.01) |
| A61B 3/10 | (2006.01) |
| G06T 7/00 | (2017.01) |
| G01J 3/28 | (2006.01) |
| A61B 5/00 | (2006.01) |
| G16H 30/40 | (2018.01) |
| G16B 40/00 | (2019.01) |
| G06V 10/58 | (2022.01) |

(52) U.S. Cl.
CPC .............. *A61B 3/12* (2013.01); *A61B 3/1015* (2013.01); *A61B 5/0075* (2013.01); *A61B 5/0077* (2013.01); *A61B 5/415* (2013.01); *A61B 5/4887* (2013.01); *G01J 3/2823* (2013.01); *G06T 7/0012* (2013.01); *G16H 30/40* (2018.01); *G01J 2003/2826* (2013.01); *G06T 2207/30041* (2013.01); *G06V 10/58* (2022.01); *G16B 40/00* (2019.02)

(58) Field of Classification Search
CPC ............ G01J 3/2823; G01J 2003/2826; A61B 5/0075; G06K 2009/4657
See application file for complete search history.

(56) References Cited

U.S. PATENT DOCUMENTS

| | | | |
|---|---|---|---|
| 6,937,885 B1 | 8/2005 | Lewis et al. | |
| 6,992,775 B2 * | 1/2006 | Soliz | A61B 3/12 356/456 |
| 7,394,919 B2 | 7/2008 | Rowe et al. | |
| (Continued) | | | |

OTHER PUBLICATIONS

Zhang, Aizhong, et al. "Multimodal imaging of ocular surface of dry eye subjects." Multimodal Biomedical Imaging XI. vol. 9701. International Society for Optics and Photonics, 2016 (Year: 2016).*

(Continued)

*Primary Examiner* — Dominic J Bologna
(74) *Attorney, Agent, or Firm* — Lynne M. Blank, Esq.

(57) ABSTRACT

A method performed by a multispectral or hyperspectral meibomian gland imaging device is disclosed, which comprises directing light having visible and infrared spectra from a broadband illuminator toward an everted eyelid; forming images of the everted eyelid using an imaging system; recording the images using a detection system, which separates the images into spectral channels, which include at least one visible spectral channel and at least one infrared spectral channel; displaying the recorded images to adjust the position of the subject to optimize image quality; digitally processing the recorded images to obtain spatial and spectral information; evaluating the health of at least one meibomian gland of the eyelid by analyzing the information. Also disclosed is a multispectral or hyperspectral meibomian gland imaging device, comprising a broadband illuminator directing light that covers visible and infrared spectra; an imaging system, and a detection system.

19 Claims, 17 Drawing Sheets

(56) References Cited

U.S. PATENT DOCUMENTS

| | | | |
|---|---|---|---|
| 8,224,425 B2 | 7/2012 | Freeman et al. | |
| 8,249,695 B2 | 8/2012 | Grenon et al. | |
| 8,600,484 B2 | 12/2013 | Grenon et al. | |
| 8,649,008 B2 | 2/2014 | Kashani et al. | |
| 8,654,328 B2 | 2/2014 | Tkaczyk et al. | |
| 9,002,085 B1 | 4/2015 | Solanki et al. | |
| 9,198,578 B2 | 12/2015 | Zuzak et al. | |
| 9,204,805 B2 | 12/2015 | Panasyuk et al. | |
| 9,320,439 B2 | 4/2016 | Arita et al. | |
| 9,907,471 B2 | 3/2018 | Caves et al. | |
| 9,968,285 B2 | 3/2018 | Valsan et al. | |
| 2008/0081996 A1* | 4/2008 | Grenon | A61B 5/411 600/443 |
| 2008/0267472 A1* | 10/2008 | Demos | A61B 1/00009 382/128 |
| 2011/0273550 A1 | 11/2011 | Amano et al. | |
| 2013/0131517 A1* | 5/2013 | Panasyuk | G01N 21/31 600/473 |
| 2014/0330129 A1* | 11/2014 | Grenon | A61B 5/0082 600/473 |
| 2015/0110372 A1* | 4/2015 | Solanki | G16H 30/20 382/130 |
| 2015/0138504 A1* | 5/2015 | Korb | G01B 11/06 351/206 |
| 2015/0141837 A1* | 5/2015 | Arita | A61B 5/0077 600/473 |
| 2018/0270474 A1* | 9/2018 | Liu | A61B 6/037 |

OTHER PUBLICATIONS

Zhang, Aizhong. Dynamic characterization of ocular surface with thermography and macroscopic imaging ellipsometry. University of Rochester, 2017 (Year: 2017).*

Smola, Alex J., and Bernhard Scholkopf. "A tutorial on support vector regression," Statistics and computing 14, No. 3 (2004): 199-222.

Nunez, Abel S., Michael J. Mendenhall. "Detection of human skin in near infrared hyperspectral imagery." IEEE Intl. Geo. & Remote Sensing. Symp. 2008 vol. 2, pp. II-621-624.

Pult, Heiko, and Jason J. Nichols. "A review of meibography." Optometry and Vision Science 89, No. 5 (2012): E760-E769.

Vyas, Saurabh, Amit Banerjee, Philippe Burlina. "Estimating physiological skin parameters from hyperspectral signatures." Journal of biomedical optics 18, No. 5 (2013): 057008.

* cited by examiner

MULTISPECTRAL AND HYPERSPECTRAL MEIBOGRAPHY

FIELD OF THE INVENTION

This invention relates to the field of ophthalmology, in particular, to image and evaluate the health of meibomian glands.

BACKGROUND OF THE INVENTION

Dry eye syndrome is one of the most common reasons people visit an ophthalmic hospital. Dry eye syndrome occurs when patients either cannot secrete enough tears or their tear quality is not good enough. Tear film is a thin, moist film anterior to the corneal epithelial cells, which forms the interface of an eye with the ambient air, and it's essential to ocular surface health. Tear film thickness is reported to be around 3 μm. Tear film consists of three layers from posterior to anterior: the mucous layer, the aqueous layer, and the lipid layer. The mucous layer forms a viscoelastic matrix to stabilize the tear film on the corneal epithelium, and the mucins are secreted by the goblet cells in the conjunctiva. The aqueous layer is the major watery part of the tear film, which contains a number of nutrients and proteins. The aqueous layer is secreted from the lacrimal gland, and it is essential for spreading of the tear film and regulating tear osmolarity. The anterior lipid layer thickness is usually in the order of 1 to 100 nm. Lipids are secreted by the meibomian glands, which are embedded in the posterior tarsal plate. The lipid layer serves to reduce evaporation, and improve the tear film stability.

Meibomian glands are modified sebaceous glands, each about 3~4 mm in length, approximately vertically lined up inside the tarsal plates of both eyelids. There are about twenty-five to forty meibomian glands in the upper eyelid and about twenty to thirty in the lower eyelid. Meibomian glands are holocrine glands with racemose morphology. Each meibomian gland has a tubuloacinar structure, comprising a central duct with an orifice adjacent to the mucocutaneous junction of the eyelid, and acini connected to the central duct through ductules. The functional cells of a meibomian gland are meibocytes, which are modified sebaceous cells, forming clusters in each acinus. Each meibocyte synthesizes and secretes lipids, also known as meibum. During each blink, the muscle of Riolan may compress the meibomian gland ductules, causing meibum secretion. The secreted meibum passes through the ductule, the lumen of the central duct, and forms the lipid layer of the tear film after exiting through the orifice of a meibomian gland.

Generally speaking, dry eye syndrome can be divided into two main categories, aqueous deficient dry eye and evaporative dry eye. Meibomian gland dysfunction is the most common form of evaporative dry eye. Abnormality in the meibum secretion, or the obstruction of the orifice of the central duct could lead to meibomian gland dysfunction. Chronic meibomian gland dysfunction might result in meibomian gland atrophy.

Meibography is a noninvasive, in vivo imaging technique to directly present meibomian gland morphology. Usually, an eyelid is everted with fingers or an eyelid everter to expose the palpebral conjunctival surface to an imaging device. Meibography uses the differences in absorption, translucency, reflectance and scattering of light by the meibomian glands, compared to adjacent tissues, to form an image with high enough contrast to examine the meibomian glands distribution within the upper and lower eyelids.

Traditionally, there are two types of meibography, one with transillumination, and the other with direct illumination. With transillumination, an eyelid is everted over an illuminator, and the light transmitted through the eyelid is imaged. With direct illumination, an everted eyelid is directly illuminated by an infrared light source in a non-contact manner, and the reflected light off the eyelid is imaged.

Meibography was invented by Tapie in 1977 based on clinical tests. Later, infrared light was used to enhance the contrast. The early meibographers usually employed transillumination. In 2008, Arita et al. reported a non-contact meibography system that uses direct illumination to collect reflection images of the everted eyelid. Later, more direct-illumination, non-contact meibographers have been developed, partly because the direct-illumination type is more comfortable for the patients during measurements compared with the earlier transillumination type.

Further, images of the lid margin have been used to directly inspect individual meibomian gland orifices at the inner side of the eyelids close to the base of eyelashes. Obstruction of the meibomian gland orifices by solidified lipids might lead to meibomian gland dysfunction, or even meibomian gland atrophy.

However, in the prior art, meibography is usually done with a limited spectrum, most commonly using near infrared light, such as described in U.S. Pat. Nos. 8,249,695, 8,600,484, 9,320,439, and U.S. Pat. Application 20110273550, and the final resultant image of the meibomian glands are black and white grayscale images. Even if pseudocolor images are used, the pseudocolor images are generated by assigning different colors to different gray levels of the black and white images, or the pseudocolor images are used to denote temperature difference in thermal imaging. These grayscale-based pseudocolor images do not contain spectral properties, and could not provide more information for diagnosis than the original grayscale image. The restriction of the light in the infrared spectrum limits the retrievable information of the meibomian gland images and potentially loses some critical pathological information.

Multispectral and hyperspectral imaging systems combine imaging with spectroscopy, hence both spatial and spectral properties of the object could be investigated.

Multispectral imaging captures image data of certain object areas in several spectral bands. Usually spectral filters and different detectors that are sensitive to particular wavelength ranges are employed to generate a number of spectral bands. The total number of spectral bands is usually fewer than 20.

Hyperspectral imaging has a lot more spectral channels than multispectral imaging and usually hundreds of spectral channels are used. Each resultant hyperspectral image is a three-dimensional data cube, known as a "hypercube", with two spatial dimensions (x, y), and one spectral dimension λ.

Even though there is no consensus on the number of spectral bands to clearly distinguish hyperspectral imaging from multispectral imaging, hyperspectral imaging generally captures a continual spectrum, with more spectral bands and higher spectral resolution, compared to multispectral imaging.

Multispectral and hyperspectral imaging techniques have been used in the prior art in medical imaging to inspect and diagnose diabetes, tumor, heart tissue ablation, fundus health and retinal diseases, etc, as described in U.S. Pat. Nos. 6,937,885, 6,992,775, 8,224,425, 8,649,008, 8,654,328, 9,002,085, 9,198,578, 9,204,805, 9,907,471, 9,968,285, etc, and they could also be used for other application such as biometric sensing, as disclosed in U.S. Pat. No. 7,394,919, etc.

However, there is still a need of a method and instrument to apply principles of multispectral and hyperspectral imaging to meibomian glands for dry eye diagnosis, with both visible and infrared spectra. Multispectral and hyperspectral meibography could bridge a significant gap between meibomian glands morphology and key palpebral tissue information such as vascular distribution, etc. Further, the introduction of polarization control to meibography could minimize superficial surface reflectance and provide more information for diagnosis.

SUMMARY OF THE INVENTION

It is an object of this invention to combine imaging with spectroscopy to extend the scope of meibography. Integration of spatial and spectral information enables a comprehensive analysis of meibomian glands.

It is another object of this invention to not only use infrared light, but simultaneously use visible light as well in meibography.

It is another object of this invention to provide a model of the eyelid as a multilayer structure with characterization parameters of each layer to investigate its absorption, reflection, transmission and scattering properties.

It is another object of this invention to provide a hyperspectral meibography system to inspect core components concentrations in different layers of the eyelid, such as the melanin, collagen, lipids concentrations in conjunctival epithelium, meibomian glands, etc.

It is another object of this invention to use machine learning methods, such as support vector machines and artificial neural networks, to estimate characterization parameters of the eyelid, and evaluate the eyelid health based on both spatial and spectral information.

It is also an object of this invention to introduce polarization control to meibography.

It is yet another object of this invention to present the interconnection of the palpebral vasculature and meibomian glands by image fusion with the vascular distribution in the visible spectrum and the meibomian gland distribution in the infrared spectrum.

It is still another object of this invention to provide a handheld meibographer to conveniently inspect the meibomian gland morphology and the eyelid margin health.

The present invention relates to a method performed by a multispectral or hyperspectral meibomian gland imaging device, and the method comprises directing light from a broadband illuminator toward at least a portion of an everted eyelid of a subject, and the light covers visible and infrared spectra; forming images of the everted eyelid using an imaging system; recording the images using a detection system, which separates the images into a plurality of spectral channels with optical filters or a dispersive optical element, and the plurality of spectral channels comprise at least one visible spectral channel and at least one infrared spectral channel; displaying the recorded images to adjust the relative position of the subject to optimize the image quality; digitally processing the recorded images to obtain spatial and spectral information; evaluating health of at least one meibomian gland of the eyelid by analyzing the spatial and spectral information. And the digital processing further comprises image preprocessing, which includes reflectance calibration, transmittance calibration, image smoothing, contrast enhancement, and removal of illumination nonuniformity; feature extraction, in which the original data dimensionality is reduced and the most important subset of the original data is obtained to extract relevant feature information of the everted eyelid; segmentation, in which a region of interest (ROI) of meibomian glands is designated and separated in the images; parameter estimation, in which characterization parameters of the everted eyelid are estimated; and evaluation, in which pathological attributes and conditions are evaluated, including a percentage of meibomian gland coverage within the ROI, the meibomian gland atrophy, meibomian gland thickness and tortuosity.

The invention also discloses a multispectral or hyperspectral meibomian gland imaging device, which comprises a broadband illuminator to direct light toward at least a portion of an everted eyelid of a subject, and the light covers visible and infrared spectra; an imaging system to form images of the everted eyelid; and a detection system, which separates the images into a plurality of spectral channels with optical filters or a dispersive optical element, and the plurality of spectral channels comprise at least one visible spectral channel and at least one infrared spectral channel.

DETAILED DESCRIPTION OF THE INVENTION

In the prior art, direct illumination or transillumation meibography are done with infrared spectrum (most commonly with near infrared spectrum), and the resultant image is a black and white grayscale image. In this invention, meibography is done with broadband imaging, covering visible and infrared spectra. Multispectral and hyperspectral meibography systems combine imaging with spectroscopy to measure not only spatial but also spectral properties of the eyelids.

Figure 1:
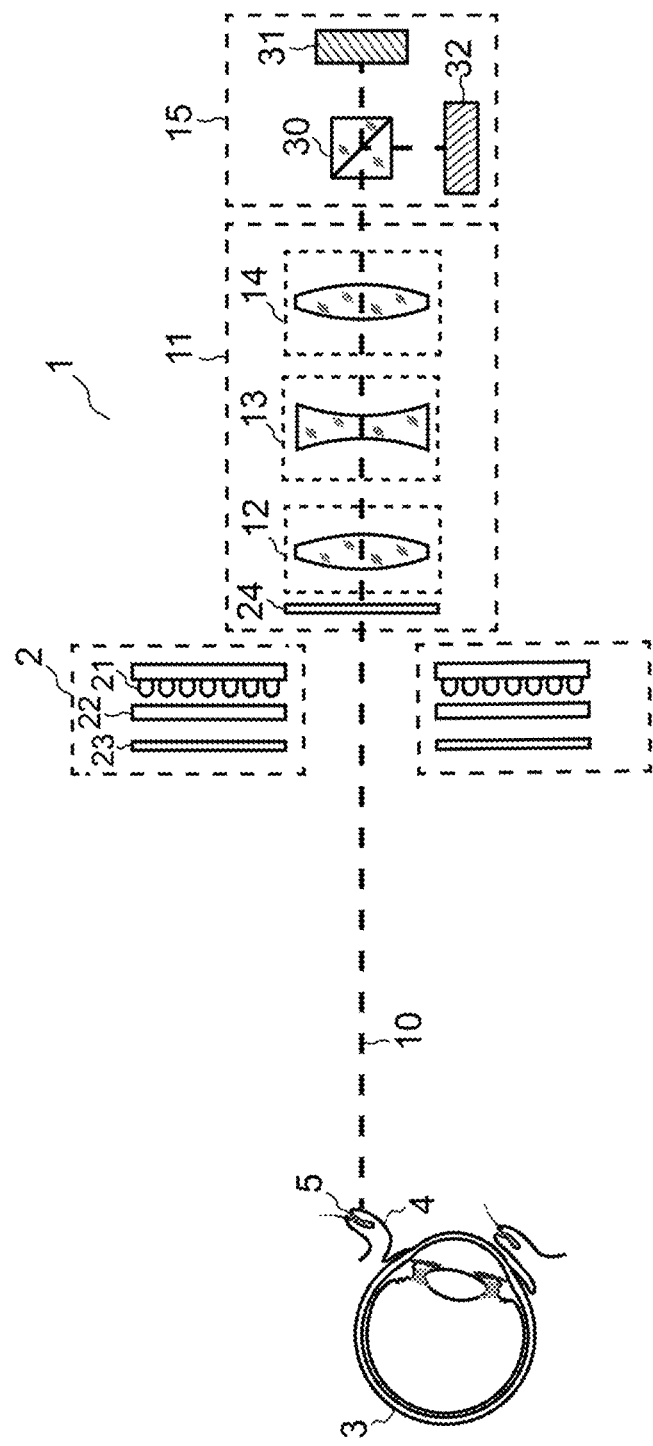
FIG. 1 illustrates the layout of one embodiment of a multispectral meibomian gland imaging device with direct illumination.

FIG. 1 illustrates one preferred embodiment of a multispectral meibography device 1 with direct illumination. A broadband illuminator 2 directs light toward at least a portion of an everted eyelid 4 of an eye 3. Preferably, the illuminator 2 comprises a broadband light-emitting diode (LED) array 21, and a translucent optical diffusing structure 22 to distribute the illuminator output light more uniformly. The LED array 21 covers both visible and infrared spectra. One embodiment of the illuminator has an annular shape with a central opening to allow light to pass through. Optionally, there is a polarizer 23 to polarize the illumination light. The embodiment of the polarizer 23 could be a linear polarizer, a circular polarizer, or polarizers of other polarization states. Meibomian glands 5 are embedded within the eyelid 4. In order to reveal meibomian glands, typically, an everted eyelid is used in meibography. As used herein, the term "everted eyelid" may be construed to mean an eyelid with partial or complete exposure of the palpebral conjunctival surface or the eyelid margin. Part of the reflected and back scattered light from the eyelid is collected by an imaging system 11, with an optical axis 10. The imaging system 11 could have many different embodiments, FIG. 1 presents one preferred embodiment of 11, comprising a positive lens group 12, a negative lens group 13, and a positive lens group 14. Optionally, there is a polarization analyzer 24 in the imaging system 11. In FIG. 1, the optional analyzer 24 is placed in front of all the lens groups. Preferably, the polarization states of the polarizer 23 and the analyzer 24 are appropriately chosen in order to minimize the surface reflection from the superficial layer of the eyelid, no matter whether the eyelid is everted or not. If the eyelid is everted, glares specularly reflected from the palpebral conjunctival surface could be avoided with proper polarization states of 23 and 24. For example, if both 23 and 24 are of linear polarization, they could be of orthogonal polarization states, and form a cross-polarization pair. If both 23 and 24 are of circular polarization, they could be of the same polarization states. In some embodiments, the analyzer 24 is of varying polarization states, and the embodiment of a varying polarization analyzer could be a rotating polarizer or a liquid crystal tunable filter, etc. After passing the imaging system 11, light reaches a detection system 15, and in one embodiment, the detection system comprises a dichroic beamsplitter 30, one visible detector 31 and one infrared detector 32. The dichroic beamsplitter 30 splits the light into one visible branch and one infrared branch to match the detectors. Note that the optional analyzer 24 could also be placed in the detection system 15, instead of the imaging system 11.

In some embodiments, if the illuminator 2 directs light at a large incident angle close to the Brewster's angle, which is about 54~55° for the conjunctiva, the reflected light will have a high degree of polarization even if the optional polarizer 23 is removed. An analyzer 24 of appropriately chosen polarization state could still be used to minimize the eyelid surface reflection.

In some embodiments, the illuminator 2 could also comprise a tunable narrow band filter or a dispersive optical element to adjust the illumination spectrum. The tunable narrow band filter could be narrow band filters mounted in a rotating wheel, or it could be a liquid crystal tunable filter, etc. Different spectral bands alternates sequentially to control the illumination spectral output. The output of the illuminator 2 at any moment is of narrow band in these embodiments, but the entire spectral coverage is still broadband.

Figure 2:
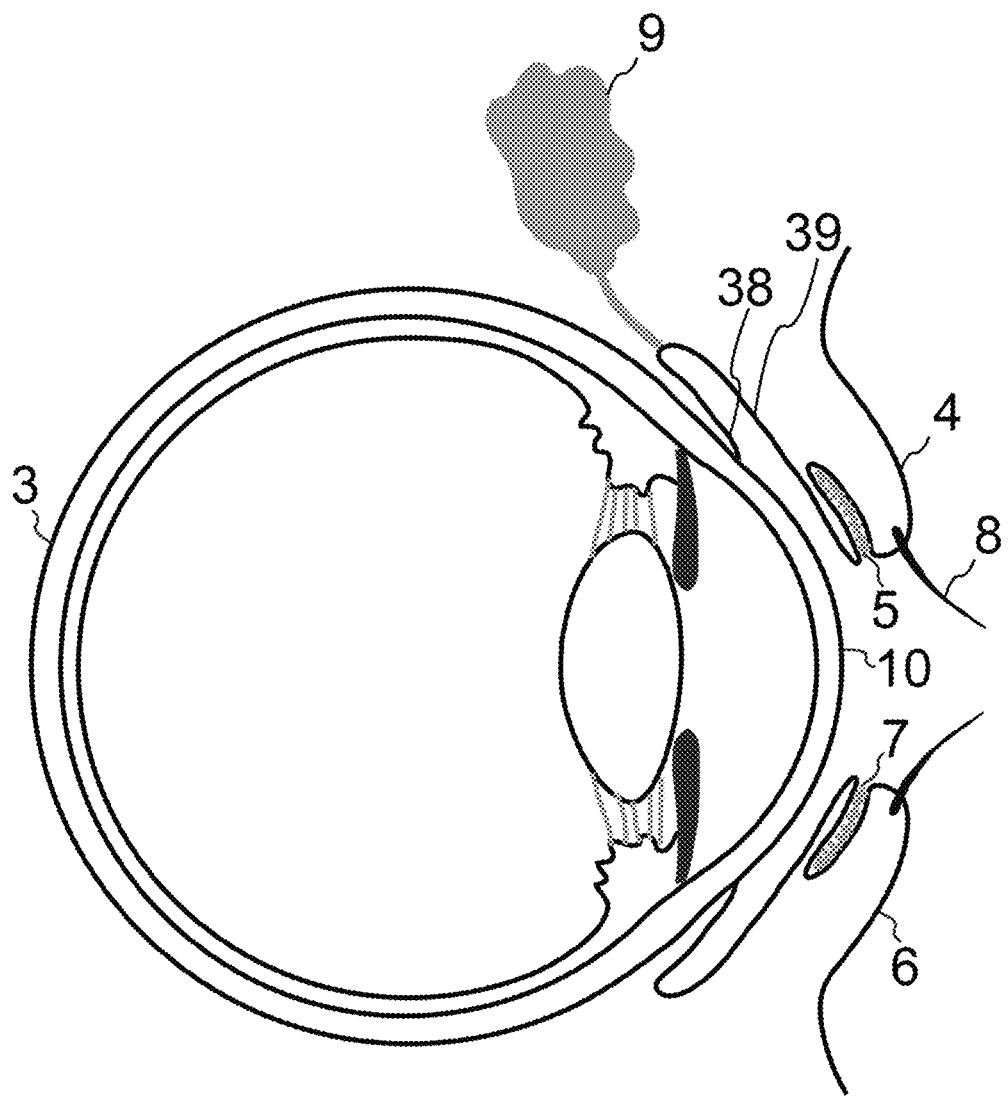
FIG. 2 presents the anatomical structures of an eye.

FIG. 2 presents the anatomical structures of the eye 3. Meibomian glands 5 are embedded in the upper eyelid 4. Similarly, meibomian glands 7 are embedded in the lower eyelid 6. The eyelashes 8 are located at the lid margin, and the base of eyelashes are slightly anterior to the meibomian gland orifices. A lacrimal gland 9 is located at the upper lateral region of each orbit. Secretory ducts of the lacrimal gland directs aqueous tears to the ocular surface and forms the aqueous layer of the tear film. The bulbar conjunctiva 38 and the palpebral conjunctiva 39 forms a conjunctival sac, which serves as a tear reservoir.

Figure 3:
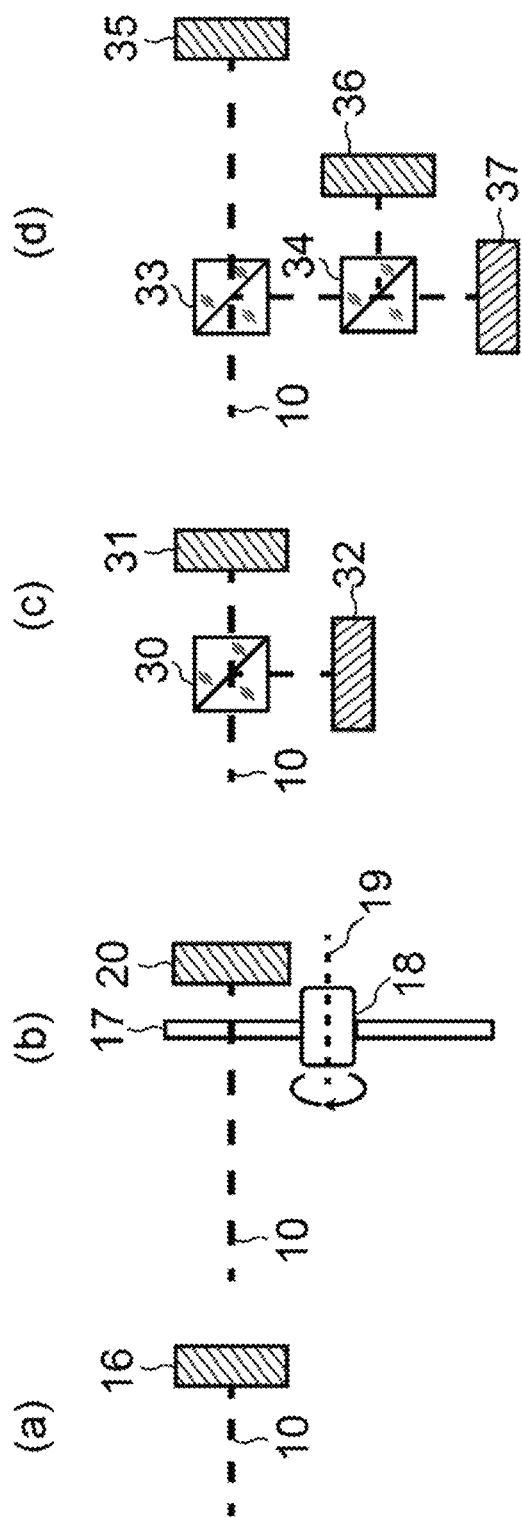
FIG. 3 shows four different embodiments of the detection system.

FIG. 3 presents four different embodiments of the detection system 15. FIG. 3(a) is a single multispectral detector 16, with pixels covering both visible and infrared spectra. For example, the detector 16 could have four different types of pixels: red (R), green (G), blue (B) and near infrared (NIR) pixels. In FIG. 3(b), the detection system comprises a rotating spectral filter wheel 17, which has different spectral filters embedded inside. A motor 18 rotates around an axis 19, and the spectral filters in front of a detector 20 change in a cyclic order. The detector 20 is sensitive to a broad range of spectrum including visible and infrared spectra. In one embodiment, the alternating filters in the filter wheel 17 are R, G, B, NIR four types. In another embodiment, the R, G, B spectral filters are directly embedded in the detector 20, while some or all of the R, G, B spectral filters allow a portion of the NIR light to pass through, and the alternating filters in the filter wheel 17 are of visible (VIS) and NIR two types. In still another embodiment, more spectral filters with narrow transmission bands could be used to image with more spectral channels. Furthermore, in a hyperspectral imaging setup, the filter wheel 17 could be replaced by a tunable filter, which is not necessarily rotary, and the tunable filter may be an acousto-optic tunable filter, or a liquid crystal tunable filter, etc.

In FIG. 3(c), the detection system comprises a dichroic beamsplitter 30, one visible detector 31 and one infrared detector 32, as employed in FIG. 1. The dichroic beamsplitter 30 splits the light into one visible branch and one infrared branch. The visible detector 31 is responsive to the visible branch, which could be a regular detector with RGB three color channels. The infrared detector 32 is responsive to the infrared branch. In FIG. 3(d), the detection system comprises a first dichroic beamsplitter 33, which splits light into a visible branch and an infrared branch. A detector 35 is responsive to the visible branch. A second dichroic beamsplitter 34 further splits the infrared branch into two different infrared spectra: Infrared 1 ($IR_1$) and Infrared 2 ($IR_2$), and detectors 36 and 37 are responsive to $IR_1$ and $IR_2$, respectively. For example, in one embodiment, 35 is responsive to the visible branch, covering a wavelength range of 400 nm to 750 nm, with RGB three color channels; 36 is responsive to the first infrared branch $IR_1$, covering 750 nm to 900 nm; 37 is responsive to the second infrared branch $IR_2$, covering 900 nm to 1100 nm.

The embodiments of the beamsplitter(s) in FIG. 3 include but are not limited to a cube beamsplitter, a plate beamsplitter, a pellicle beamsplitter, etc.

In some embodiments, the detection system 15 comprises detectors with polarization image sensors, where the optional polarization analyzer 24 is directly formed on chip.

One preferred embodiment of the polarization image sensor to work in the visible and near infrared spectra is Sony IMX250MZR/MYR or Sony IMX253MZR/MYR sensor. The Sony polarization image sensors have a polarization analyzer 24 with four different directional polarization states. If the analyzer 24 has more than one polarization states as in the polarization image sensors, at least one pair of polarization states of the polarizer 23 in the illuminator and the analyzer 24 are chosen to minimize superficial surface reflection of an eyelid. By comparing and combining the images from different analyzers for each frame, the polarization information could be also used to extract the tissue properties.

Figure 4:
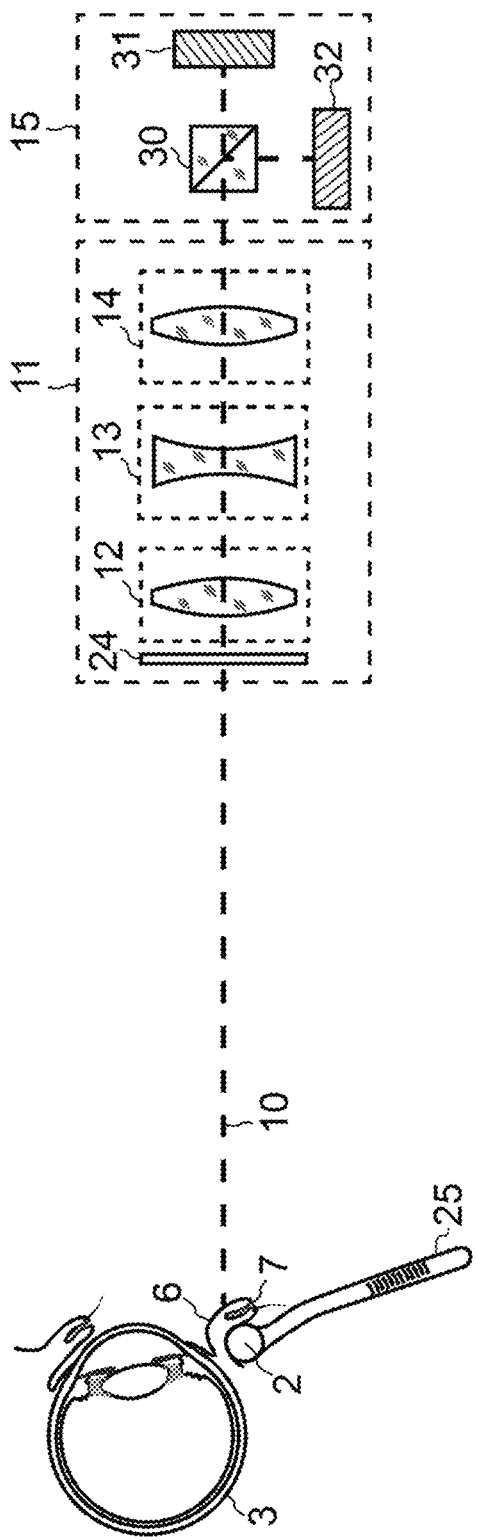
FIG. 4 illustrates one embodiment of a multispectral meibomian gland imaging device with transillumination.

FIG. 4 illustrates one embodiment of the multispectral and hyperspectral meibography device with transillumination. A broadband illuminator 2 is placed behind a cutaneous side of an everted eyelid 6, and the eyelid 6 is everted over the illuminator 2 to direct light through the meibomian glands 7. The illuminator 2 is connected to a handle 25 to be held by an operator. Part of the transmitted and forward scattered light is collected by an imaging system 11 and reaches a detection system 15.

Figure 5:
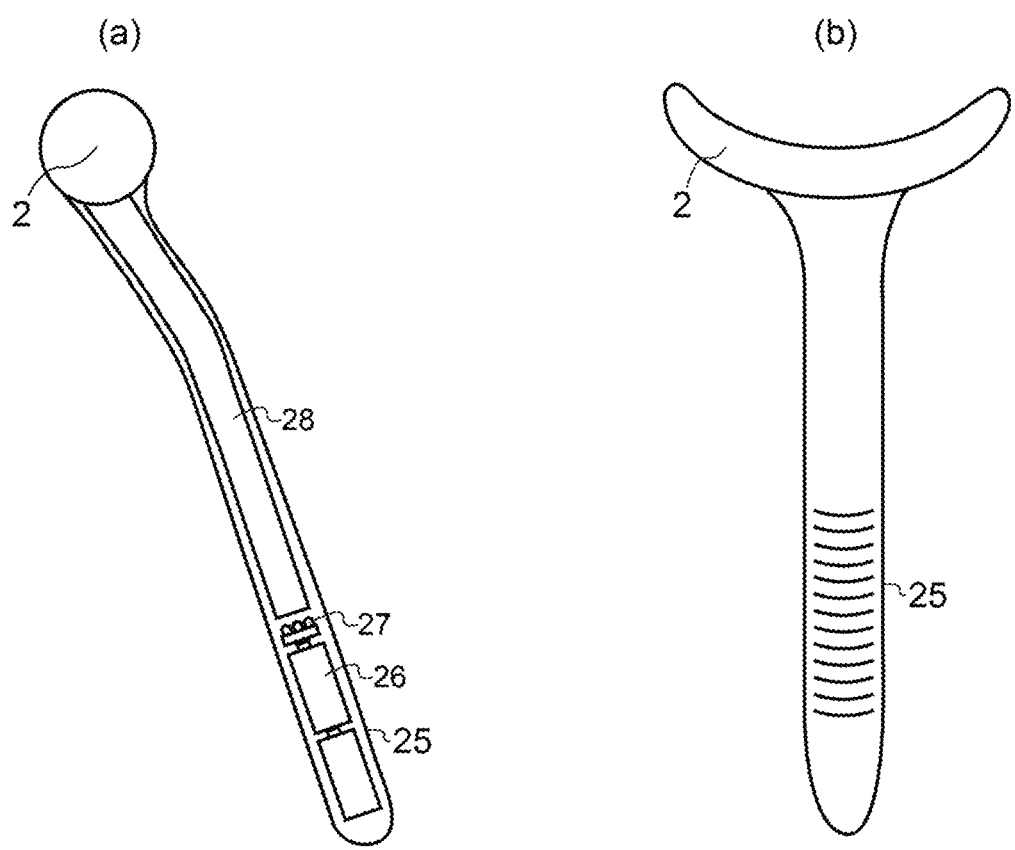
FIG. 5 presents the detailed structure of one embodiment of the transillumination illuminator.

FIG. 5 presents the detailed structure of one embodiment of the transillumination illuminator device. FIG. 5(*a*) is a side view, and FIG. 5(*b*) is a front view. In FIG. 5(*a*), batteries 26 provide electrical energy for the illuminator 2. Alternatively, a power cord (not shown) could be used to supply the electrical energy. Light is emitted by a broadband source 27, and one preferred embodiment of 27 is an array of visible and infrared LEDs. A light guide 28 transfers the broadband light to the illuminator 2. Optionally, a beam shaping system (not shown) could be inserted between the light source 27 and light guide 28, or it could be integrated within the light guide 28 to control the output light distribution. The batteries 26, the broadband light source 27, and the light guide 28 are all installed within the handle 25. Optionally, a polarizer 23 (not shown in FIG. 5) is wrapped around the illuminator 2. The optional polarizer 23 could also be placed between the light source 27 and the light guide 28, if 28 is a polarization-maintaining light guide, which can preserve the polarization state during light propagation.

FIG. 5(*b*) presents a preferred shape of the illuminator 2 for transillumination, of which the meniscus shape conforms to the contour of an eyelid to facilitate the eversion of the eyelid over the illuminator.

Sometimes, a hyperspectral imaging system is needed for a comprehensive spectral measurement. Hyperspectral imaging systems combine the spatial information with rich spectral information, which could elucidate component concentration information otherwise difficult to obtain non-invasively.

Figure 6:
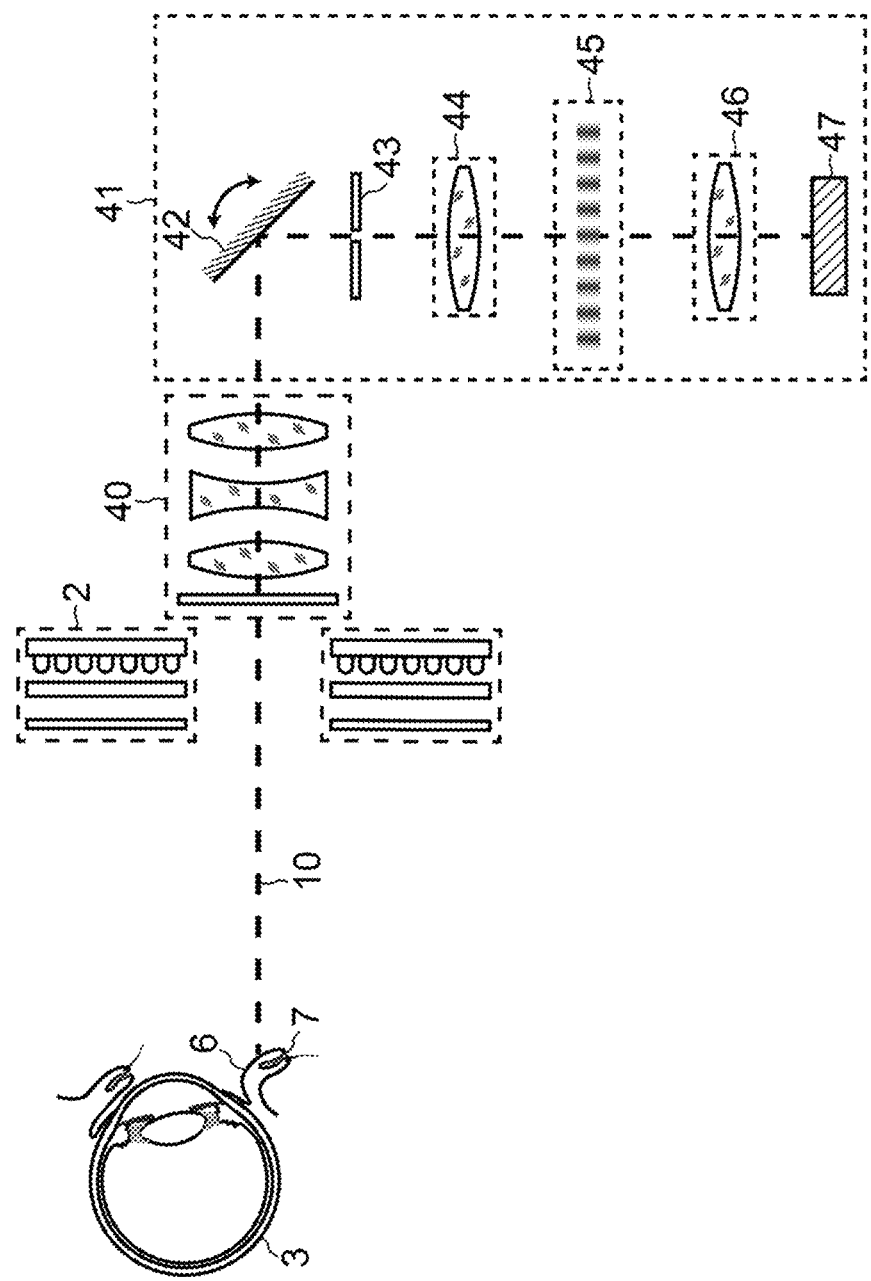
FIG. 6 presents one embodiment of a hyperspectral meibography device with a transmissive spectrometer system.

FIG. 6 presents one embodiment of a hyperspectral meibography device. A broadband illuminator 2 directs light onto an eyelid 6 of an eye 3, with meibomian glands 7 embedded within the eyelid 6. Part of the reflected light and back scattered light from the eyelid is collected by an imaging system 40, with an optical axis 10. After the imaging system 40, the detection system is a transmissive spectrometer system 41 in FIG. 6. In the spectrometer system 41, a rotary scanning mirror 42 guides light through a slit 43. One preferred embodiment of the scanning mirror 42 is a rotating polygon scanner. Preferably, the slit 43 is located at an intermediate image plane of the preceding imaging system 40 to spatially filter out a slice of the image of the eyelid 6, and maintain only one spatial dimension, in order to avoid overlap of dispersed beams from two spatial dimensions. A collimating lens group 44 turns the light from the slit 43 into collimated light before reaching a transmission grating 45. Preferably, 45 is a transmission grating, such as a volume phase holographic (VPH) transmission grating, though it could also be a diffractive lens, a prism, a Bragg grating, or other similar dispersive elements. The transmission grating 45 separates the collimated incoming beam into output beams of different wavelengths at different output angles, and the output beams from the grating 45 pass through a focusing lens group 46 and reach a detector 47. Each image frame of the detector 47 contains one spatial dimension and one spectral dimension. The detector 47 could be a charge-coupled device (CCD), a complementary metal-oxide-semiconductor (CMOS), or other functionally similar imaging recording devices. Typically, the detector could be used to obtain hundreds of spectral channels. At any moment, the detection system forms an image of one slice of the object through the slit 43. By rotating the scanning mirror 42, the entire two-dimensional object could be imaged.

Figure 7:
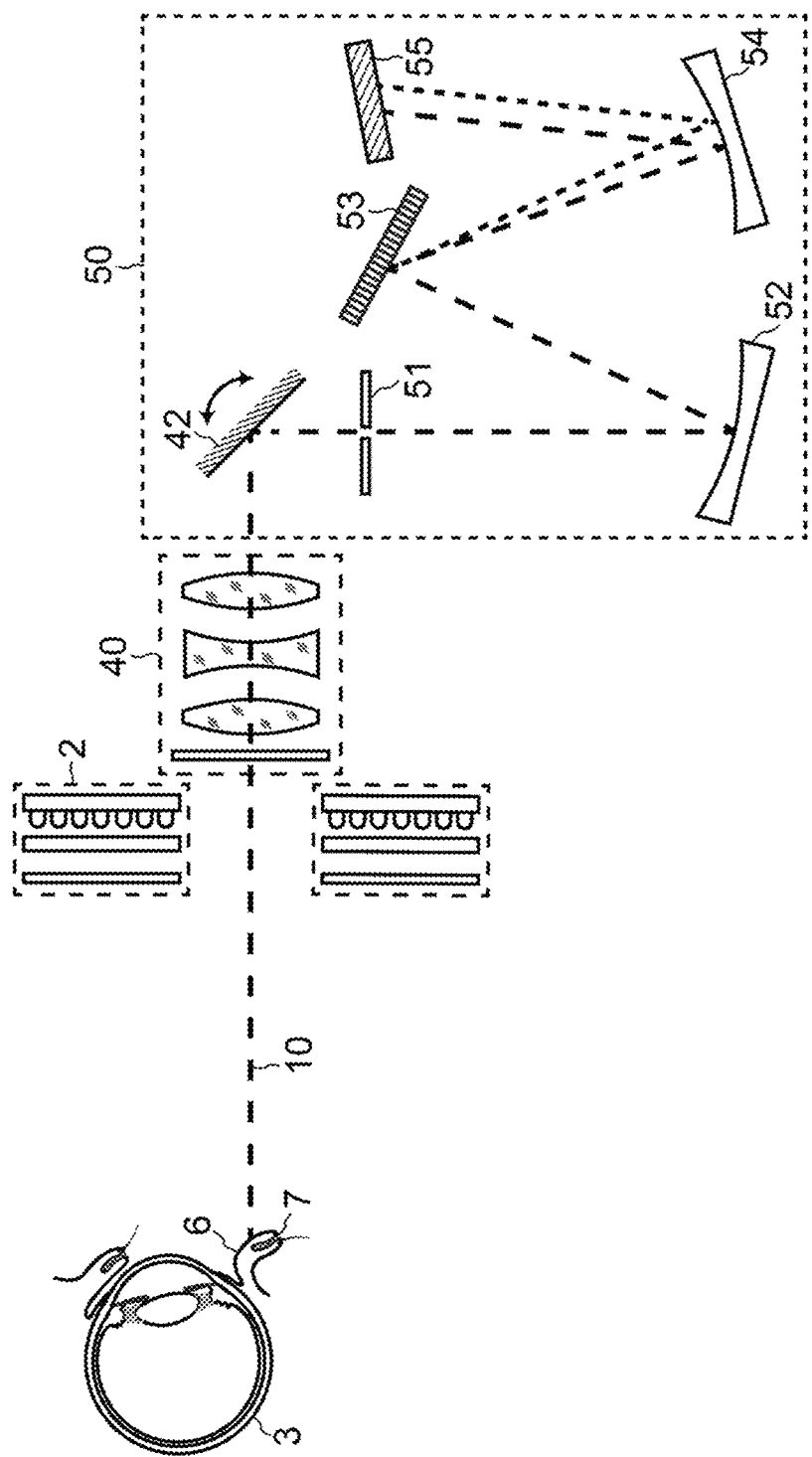
FIG. 7 presents another embodiment of the hyperspectral meibography device with a reflective spectrometer system.

FIG. 7 presents another embodiment of the hyperspectral meibography device. The illuminator 2, the imaging system 40 and the rotary scanning mirror 42 could be similar to those in FIG. 6. The spectrometer system 50 in FIG. 7 is a reflective spectrometer system, instead of a transmissive spectrometer system as in FIG. 6. The main advantage of the reflective spectrometer system is a potential broader spectral range, since a transmissive spectrometer system tends to suffer from chromatic aberrations induced by material dispersion. In FIG. 7, a Czerny-Turner configuration is illustrated as one preferred embodiment of the spectrometer system 50. A slit 51 is preferably located at an intermediate image plane of the preceding imaging system 40 to spatially filter the image of the eyelid 6 to retain only one spatial dimension. The input beam from the slit 51 is collimated by a collimating mirror 52, before reaching a grating 53. Preferably, the grating 53 is a reflective diffraction grating, though 53 could also be a holographic grating or other dispersive optical element. The grating 53 disperses light of different wavelengths into different directions, and the output beams of the grating reaches a focusing mirror 54, which directs light onto a detector 55. The detector 55 could be a CCD or a CMOS, or other recording devices.

The spectrometer system 50 in FIG. 7 is shown as a Czerny-Turner configuration, but other spectrometer configurations such as a Littrow mount, an Ebert-Fastie mount, etc could also be used. Further, the grating in FIG. 7 could be ruled on a concave or convex surface, and correspondingly, an Eagle spectrometer, a Wadsworth spectrometer, a Dyson spectrometer, or other similar configurations, could also be employed.

Note that in some embodiments, the scanning mirror 42 in FIG. 6 and FIG. 7 could also be other scanning system, such as a point-scanning whiskbroom scanner. The slit 43 or 51 is preferably replaced by a slit or a pinhole of an appropriate size to match the point-scanning whiskbroom scanner.

Furthermore, the spectrometer system could also be a Fourier transform spectrometer. The spectrum of the object is obtained from the Fourier transform of interferograms. One embodiment of the Fourier transform spectrometer has the basic setup as a Michaelson interferometer, which contains one moving mirror and one stationary mirror. The optical path difference (OPD) is modulated by the displacement of the moving mirror, so that the detected signal varies with the moving mirror displacement. With an imaging Fourier transform spectrometer, a two-dimensional interferogram for each moving mirror position could be recorded, and the Fourier transform of the interferogram variation of each pixel will reveal its spectral distribution. The spectral calculation for all the pixels in the field of view will generate a hypercube of the eyelid and adjacent tissues.

Moreover, spectral scanning methods which capture the two-dimensional spatial image in a single frame, and step through the spectral range during scanning could also be employed in multispectral and hyperspectral meibography. These spectral scanning methods could employ spectral filters in the form of rotating narrow band spectral filters, acousto-optic tunable filters, and liquid crystal tunable filters, etc. These filters could be placed on either the illumination side or the detection side of the meibography system.

Note that although in the preferred embodiments, the multispectral and hyperspectral meibography systems work in the visible and infrared spectra, these systems could also be readily extended to work in the ultraviolet (UV) spectrum as well.

During a measurement, it's preferred to display recorded images in real time to adjust the relative position of the subject, to ensure subject comfort and optimize the image quality.

It is also preferred to use a control system to control and coordinate the broadband illuminator, the imaging system, and the detection system.

The multispectral and hyperspectral meibography systems disclosed in this invention have at least two spectral channels, one in the visible spectrum and the other in the infrared spectrum. However, a multispectral system could have two to twenty, or even more spectral channels, and a hyperspectral system usually has hundreds or even more spectral channels.

Different wavelengths have different penetration depths. Near-infrared is generally used as a spectral window for deeper biological tissue measurement, since NIR spectrum penetrates deeper into the tissue than visible light (VIS), mid-infrared (MIR), and long wave infrared (LWIR). This is partly because some chromophores such as hemoglobin and melanin absorb UV and VIS strongly, and water absorbs MIR and LWIR strongly. The penetration depth is about 1 mm below the tissue surface for the visible light, and about 1 to 5 mm below the tissue surface for NIR. In multispectral and hyperspectral meibography, NIR contains more information about the deeper structures including the meibomian glands, while other wavelength bands, including the visible light, contain more information of the structures immediately below the surface.

After being recorded by the detection system, the images are digitally processed. In multispectral and hyperspectral meibography, digital processing in general comprises image preprocessing 112, feature extraction 113, segmentation 114, parameter estimation 115, and evaluation 116—five main steps. The similarities and differences of these five steps for a multispectral system and a hyperspectral system are explained in the following.

Image preprocessing 112 includes the steps to calibrate the irradiance reflectance with reference targets. This step is the same for both multispectral and hyperspectral imaging systems. Preferably, the calibration is done with a white image and a dark image. The white image is taken with a reference white panel, and preferably the reference white panel is a Spectralon white diffuse reflectance target. The irradiance reflectance could be expressed as $$\rho = \frac{DN_s - DN_{dark}}{DN_{white} - DN_{dark}} \rho_{white} \tag{1}$$

where DN stands for data number, $DN_s$ is the data number of the sample at each pixel of each spectral channel of an image sensor, and in meibography, the sample is usually part of an eyelid. $DN_{dark}$ is the data number of the dark current with the optical shutter completely closed. $DN_{white}$ is the data number of the reference white panel. $\rho_{white}$ is the irradiance reflectance of the reference white panel. For a Spectralon target, typically, $\rho_{white} > 99\%$ in the spectral range of 400 nm to 1500 nm, and $\rho_{white} > 95\%$ from 250 nm to 2500 nm.

If no reference white panel is available, the calibration could also be done with other optical materials with known reflectance properties as $$\rho = \frac{DN_s - DN_{dark}}{DN_r - DN_{dark}} \rho_r \tag{2}$$

where $\rho_r$ is the irradiance reflectance of the reference optical material, such as a BK7 glass reference plate, at the calibration wavelength, and $DN_r$ is the corresponding data number. The calibration can be repeated for a series of wavelengths, and a final curve of $\rho$ could be interpolated and extrapolated for the full wavelength range. A neutral grey reference target could also be employed to simplify the calibration process for different wavelengths.

The above reflectance calibration is mainly used for direction illumination. For transillumination, a similar procedure of transmittance calibration could be done.

Image preprocessing further includes image smoothing, contrast enhancement, and removal of illumination nonuniformity, etc. Image smoothing could be done using median filters of a properly chosen size or other smoothing algorithms Contrast enhancement, or contrast stretch, includes multiple transform methods in both spatial domain and spectral domain. Spatial contrast enhancement methods include stretching the original data number range to fill the full gray level range, with linear, nonlinear, histogram equalization, reference stretch and other related methods. Spectral contrast enhancement methods include normalization stretch, spatial domain blending, etc. Removal of the illumination nonuniformity could be partly done with the reflectance or transmittance calibration, and partly done with a high-pass filter or a homomorphic filter.

The second step of digital processing is feature extraction 113. Feature extraction aims to reduce the original data dimensionality and obtain the most important subset of the original data to extract relevant feature information of the eyelid. Similar procedure could be applied to both multispectral and hyperspectral meibography, although it's especially useful for hyperspectral meibography due to its high spectral dimensionality. Feature extraction is not an absolutely necessary step for some analysis applications, but it is preferred for multispectral and hyperspectral meibography. Commonly used feature extraction methods include principal component analysis (PCA), minimum noise fraction (MNF), independent component analysis (ICA), spectral angle mapper (SAM) and spectral information divergence (SID), etc.

In the feature extraction step, other than the raw spectral channels physically located in the detection system, some of these raw spectral channels could be combined and manipulated to generate additional "digital spectral channels" to further improve feature contrast. For example, with principal component analysis (PCA), new digital channels, i.e. the principal components, could be constructed as weighted linear combinations of the raw spectral channels.

As another example, additional digital spectral channels could be generated based on two indices. The first index is the "Difference Meibomian Gland Index" (DMGI), for a multispectral meibography device with direct illumination, $$DMGI = |R_r - R_n| \quad (3)$$

where $R_r$ and $R_n$ are the irradiance reflectance values of red and near infrared spectral channels calculated at each pixel. The irradiance reflectance includes light of both reflection and backward scattering that is collected by the device.

Similarly, for a multispectral meibography device with transillumination, $$DMGI = |T_r - T_n| \quad (4)$$

where $T_r$ and $T_n$ are the irradiance transmittance values of red and near infrared spectral channels calculated at each pixel. The irradiance transmittance includes light of both transmission and forward scattering that is collected by the device.

The second index is the "Normalized Difference Meibomian Gland Index" (NDMGI), and for direct illumination, $$NDMGI = |(R_r - R_n)/(R_r + R_n)| \quad (5)$$

Similarly, for transillumination, $$NDMGI = |(T_r - T_n)/(T_r + T_n)| \quad (6)$$

These indices are evaluated at each pixel, so an entire frame of a meibomian gland image can be analyzed to potentially enhance the contrast of the meibomian glands with respect to neighboring tissues. Thus each frame based on either index could be considered as an additional digital spectral channel. Other indices containing visible and near infrared spectra information could also be used to increase the contrast and generate additional digital spectral channels.

If a hyperspectral imaging setup is used, the DMGI and NDMGI indices could be evaluated at narrower, more specific spectral bands.

Different spectral channels emphasize different features in clinically obtained multispectral and hyperspectral images of the eyelid, no matter whether they are the raw spectral channels or the additional digital spectral channels. Experimental results demonstrate that infrared spectral channels tend to have relatively high image contrast of the meibomian glands, which is suitable to study the meibomian glands distribution and morphology. Visible spectral channels have low image contrast of healthy meibomian glands, and this might be the primary reason that meibography was most commonly done in the infrared spectrum in the prior art. But visible green and blue color channels tend to have high contrast of the blood vessels with adjacent tissues, and usually the green color channel tends to have the highest image contrast of vasculature. The visible red color channel tends to have low contrast and the red color channel data numbers of an image of an everted eyelid tend to be much higher than the green and blue channels, due to stronger reflectance by the blood vessels and the collagen fibers in the red color channel However, clinical studies demonstrate that in some patients with meibomian gland dysfunction (MGD), the dilated central duct filled with excess meibum could enhance the contrast of the meibomian glands with adjacent tissues, even in the visible spectrum. The increased meibomian gland contrast for MGD patients is especially prominent close to the lid margin. Further, when there is meibomian gland obstruction at the gland orifice, the image contrast at the visible blue and green color channels tend to increase at the orifices. Hence, although the meibomian gland image contrast tends to be low in the visible spectral channels, visible spectral images might contain critical pathological information to distinguish a MGD patient from a normal subject.

Multispectral and hyperspectral imaging enables image fusion to reveal more biological features. For example, image fusion with at least one visible spectral channel and at least one infrared spectral channel could be used to assess the interconnection of palpebral vasculature and meibomian glands, with visible channels to present the blood vessels and infrared channels to present the meibomian glands. For example, a pair of (G, IR) two grayscale images could be fused.

Further, any three different spectral channels, whether they are the raw spectral channels or additional digital spectral channels, could be fused to generate false color images, which would help to visualize the multispectral and hyperspectral images. For example, the visible red channel, and two infrared spectral channels could be groups as (R, $IR_1$, $IR_2$) to replace conventional (R, G, B) three color channels in an image to generate a false color image. Each of the (R, $IR_1$, $IR_2$) channel is a two-dimensional gray scale image. Similarly, three infrared spectral channels ($IR_1$, $IR_2$, $IR_3$) could be used to generate an infrared-only false color images of meibomian glands. If false color images to overlay the vasculature with the meibomian glands is preferred, (G, $IR_1$, $IR_2$), (B, $IR_1$, $IR_2$), or (G, B, $IR_2$) could be used.

Additional digital spectral channels could also be used in the false color images. For example, if the detection system only has red (R) and infrared (IR) two spectral channels, a third digital spectral channel of R−IR, or (R−IR)/(R+IR) could be generated, and (R, IR, R−IR) or [R, IR, (R−IR)/(R+IR)] could be used in the false color images. As another example, if the detection system has RGB three visible channels, and $IR_1$, $IR_2$ two infrared channels, any three channels out of the available raw and additional digital spectral channels could be combined to generate false color images, such as [G, $IR_2$, (R−$IR_1$)/(R+$IR_1$)], [$IR_1$, $IR_2$, ($IR_1$−$IR_2$)/($IR_1$+$IR_2$)], [B, $IR_1$, ($IR_1$−$IR_2$)/($IR_1$+$IR_2$)], etc.

Hence, feature extraction 113 comprises (108) generating additional digital spectral channels, by combination of at least two of a plurality of spectral channels of the detection system; (109) generating false color images of the everted eyelid by selecting and combining spectral channels out of a plurality of spectral channels of the detection system and the additional digital spectral channels. Typically, three spectral channels are selected for a false color image.

Figure 8:
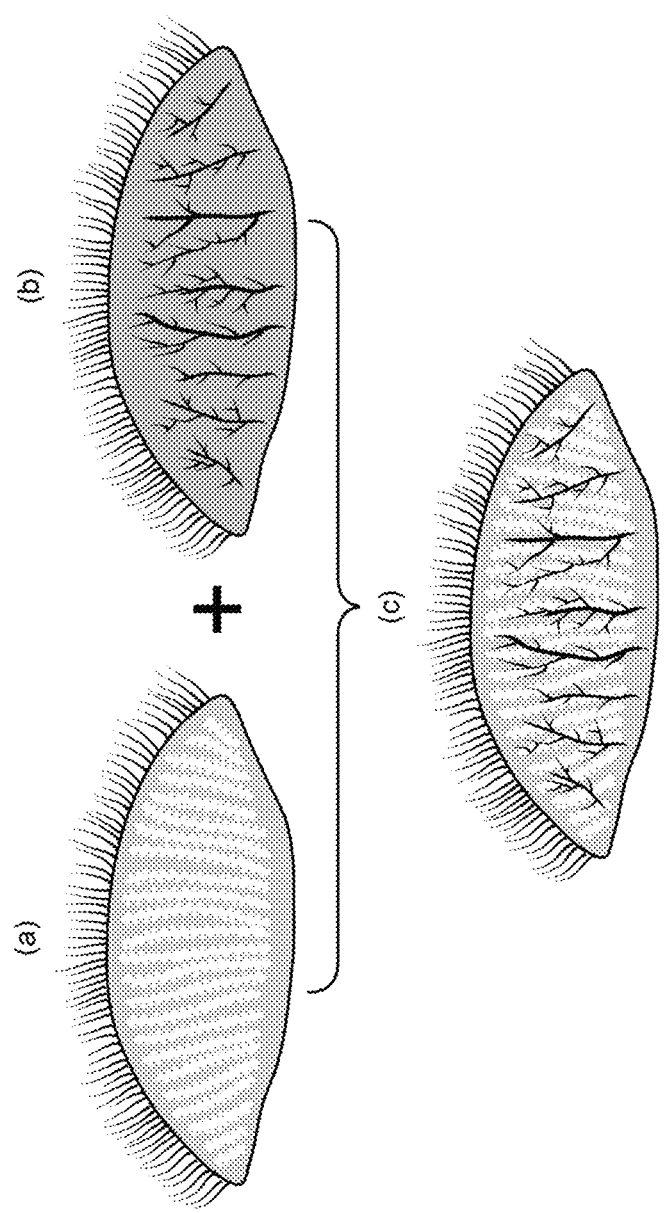
FIG. 8 presents one embodiment of image fusion of an upper eyelid by multispectral and hyperspectral meibography.

FIG. 8 presents one embodiment of image fusion of an upper eyelid by the disclosed multispectral and hyperspectral meibography. At least one infrared spectral channel is used for imaging of the meibomian glands as shown in FIG. 8(a). At least one visible spectral channel, preferably visible green channel, is used for imaging of the palpebral vascular distribution as shown in FIG. 8(b). FIG. 8(c) is a fused image to show both physiological features.

Figure 9:
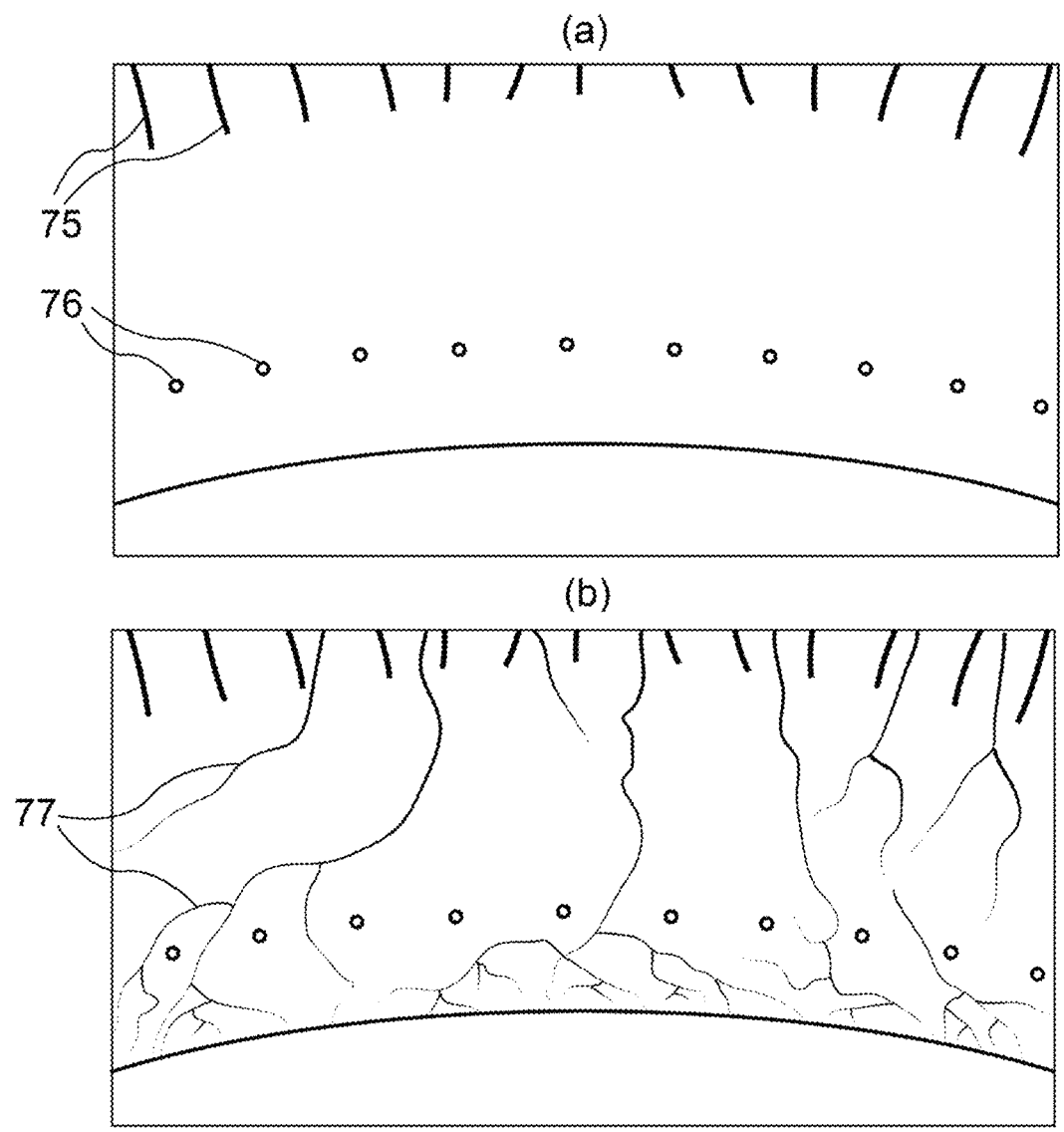
FIG. 9 presents a comparison of the images of a healthy eyelid margin, and an eyelid margin of a patient with meibomitis, which presents increased vascularity around meibomian gland orifices.

Image fusion is especially helpful for the diagnosis of meibomitis, since there could be increased vascularity of the eyelid margin, invading the orifices of meibomian glands in some patients. FIG. 9 presents part of an image of the eyelid margin to emphasize meibomian gland orifices. FIG. 9(a) presents a healthy eyelid margin, where the palpebral vasculature close to the eyelashes 75 and the meibomian gland orifices 76 is barely visible. FIG. 9(b) presents the eyelid margin of a patient with meibomitis, a subgroup of MGD, where the palpebral blood vessels 77 close to the meibomian gland orifices are clearly recorded by the visible spectral channels. The infrared spectral channels can further help to locate the meibomian gland orifices.

Note that direct illumination is preferred, if both the palpebral vasculature and the meibomian gland distribution are to be studied simultaneously. If transillumination is used, the entire thickness of an eyelid will be illuminated through, and the scattering of all different layers of blood vessels and adjacent tissues inside the eyelid will generate a relatively uniform background, and largely wash out the vascular distribution information in the visible channels, and the resultant transillumination image is mostly of meibomian glands only. In the visible spectrum, the resultant transillumination image is a low contrast image of slightly dark meibomian glands on a red background.

After feature extraction, segmentation 114 is the next step to designate and separate the region of interest (ROI) from the remaining parts of the images. In meibography, segmentation is the step to isolate a portion of an image that correspond to the meibomian glands. Typically, ROI is a continuous region including the spaces between adjacent meibomian glands. The remaining parts of the image, such the eyelashes, facial skin, the ocular surface, etc are masked out. In both multispectral and hyperspectral systems, segmentation can be carried out based on spectral and spatial analysis or feature recognition. Segmentation could be also be done with methods such as support vector machines (SVM) and artificial neural networks (ANN), etc., to classify ROI and non-ROI areas.

Once the region of interest of the meibomian glands is selected after segmentation, the next step is parameter estimation 115, where characterization parameters are estimated. Due to the availability of spectral channels, usually hyperspectral systems can analyze and estimate a lot more parameters than multispectral systems. For multispectral meibography, a basic characterization parameter could be a Boolean parameter of 0 or 1 to distinguish image pixels representing part of a meibomian gland and non-meibomian gland pixels within the ROI, hence the meibomian gland morphology could be obtained for diagnosis. For hyperspectral meibography, this step could generate estimation of detailed characterization parameters of different structures of the eyelid. These key characterization parameters include melanin, collagen and lipids concentration, blood vessel oxygenation, etc. Further, meibomian gland distribution and vascular distribution could be mapped based on these characterization parameters. Supervised or unsupervised pixel and subpixel based methods could be used for hyperspectral analysis. A number of regression and classification methods based on parametric methods or non-parametric machine learning methods such as support vector machines (SVM) and artificial neural networks (ANN), etc. could be used for meibography.

The last step of digital processing is evaluation 116. This step is applied to both multispectral and hyperspectral systems. Pathological attributes and conditions, such as the percentage of meibomian gland coverage within the ROI, the meibomian gland atrophy, meibomian gland thickness and tortuosity, etc., could be evaluated to generate a diagnostic result of the meibomian gland health. Further, in a hyperspectral meibography system, more parameters, such as blood oxygenation, lipids and collagen concentration, etc., could enable comprehensive evaluation of the meibomian glands and adjacent structures.

The entire digital processing of the five steps 112-116 could be automated, but the final evaluation and diagnosis could be done by medical professionals, if preferred. The evaluation of meibomian glands health comprises (110) assessing an interconnection of palpebral vasculature and at least one meibomian gland by image fusion with at least one visible spectral channel and at least one infrared spectral channel; (111) evaluating meibomian gland orifice obstruction and palpebral vasculature of the everted eyelid with images of an eyelid margin.

In the following, a preferred meibography parameter estimation method is disclosed in detail, which includes a forward model and an inverse model. The forward model is based on the optical reflection, transmission, scattering and absorption properties of the eyelid physiological structures to predict the signal output of the detection system; and the inverse model is based on a parametric method or a machine learning method to estimate eyelid characterization parameters from detected signals. Those skilled in the art could readily extend other similar procedures to meibography.

Figure 10:
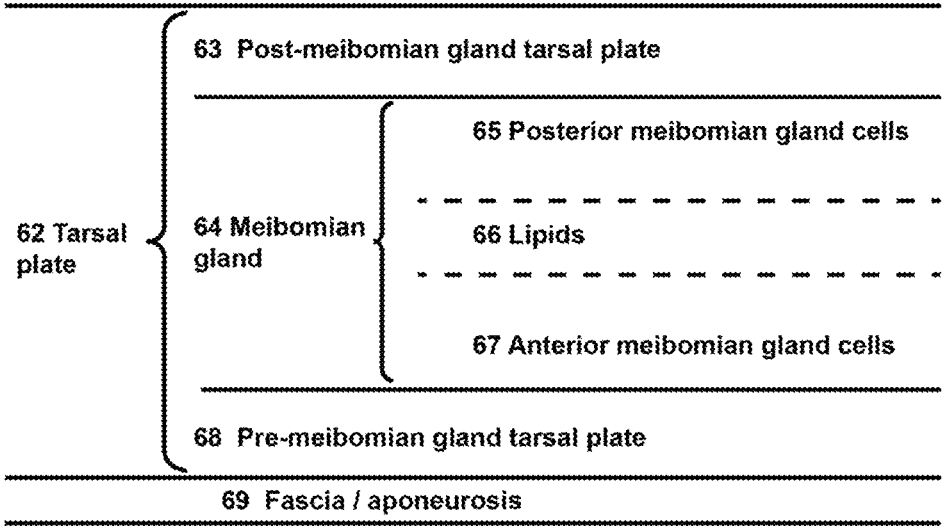
FIG. 10 presents a model of an eyelid as a multilayer structure.

In the forward model, the everted eyelid is molded as a multilayer structure as shown in FIG. 10. Note that the positional words "anterior" and "posterior", and prefixes "pre-" and "post-" are the opposite of normal use to be consistent with the anatomical terminology since the eyelid is everted. The layers of the eyelid are labeled from the conjunctival side above to the cutaneous side below in sequence: the conjunctival epithelium 60, the conjunctival stroma 61, the tarsal plate 62, the fascia or aponeurosis 69, the orbicularis oculi muscle 70, the hypodermis 71 of the eyelid, the dermis 72 of the eyelid, the living epidermis 73 of the eyelid, and the stratum corneum 74 of the epidermis of the eyelid. 69 is the fascia of the lower eyelid retractor or the levator aponeurosis of an upper eyelid. For the area of the everted eyelid that contains a meibomian gland, the tarsal plate could be further divided into the post-meibomian gland tarsal plate 63, the meibomian gland 64, and the pre-meibomian gland tarsal plate 68. The post-meibomian gland tarsal plate 63 includes the loose connective tissue. In the preferred method, the meibomian gland 64 is further divided into three sublayers, the posterior meibomian gland cells 65, the lipids or meibum 66, the anterior meibomian gland cells 67. The skin of an eyelid including 72-74 is about 0.5~1 mm thick, and the total thickness of a healthy eyelid is about 4~5 mm. The total thickness of an eyelid could vary significantly with pathological conditions, such as a chalazion, or a sty, etc.

The above division of the layers and sublayers is meant to represent the core structures of the eyelid for optical modeling purposes, hence it is not an exact anatomical representation. If necessary, each layer can be divided further into sublayers, and additional anatomical layers could be added. For example, the living epidermis 73 of an eyelid could be further divided into four sublayers: stratum basale, stratum spinosum, stratum granulosum, and stratum lucidum, from the dermis side to the stratum corneum side.

For direct illumination on an everted eyelid, the layers beneath the tarsal plate 62, i.e. layers 69-74, contribute minimally to the reflected and back scatted images, and could be ignored, if the induced errors are acceptable. For transillumination, all the layers and sublayers are analyzed, though some structures may be simplified. From the perspective of computing efficiency and robustness, a system with a small number of parameters is preferred, hence direct illumination is preferred for hyperspectral meibography.

In the forward model, an input vector space containing biological characterization parameters of the eyelid tissues, is mapped to an output vector space of the spectral components of the hyperspectral meibography system, $$p \rightarrow x, \ x = f(p) \tag{7}$$

f is the forward mapping function, p is an input vector of eyelid characterization parameters, and $p=[p_{th0}, p_{th1}, p_{th2}, p_{col}, p_{mel}, p_{car}, p_{bil}, p_{myo}, p_{lip}, p_w, p_{bld}, p_o]$, and each component of the vector p is a scalar to characterize a certain feature of the eyelid, i.e. any k-th component $p_k \in \mathbb{R}^1$. $p_{th0}$ is the post-meibomian gland (post-MG) tarsal plate thickness, $p_{th1}$ is the meibomian gland layer thickness, $p_{th2}$ is the pre-MG tarsal plate thickness, $p_{col}$ is the collagen concentration in a layer, $p_{mel}$ is the melanin concentration, $p_{car}$ is the β-carotene concentration, $p_{bil}$ is the bilirubin concentration, $p_{myo}$ is the myosin concentration, $p_{lip}$ is the lipids concentration, $p_w$ is the water volume fraction, $p_{bld}$ is the blood volume fraction, $p_o$ is the oxygenation saturation. Preferably, a series of the thicknesses of layers, and core components concentrations in each layer are modeled to form the input vector p. x is the calibrated irradiance reflectance or the preprocessed data number of each spectral channel at a spatial point. $x=[x(\lambda_1), x(\lambda_2), \ldots, x(\lambda_{M-1}), x(\lambda_M)]$, and the subscript "M" is the total number of multispectral or hyperspectral channels, and $x \in \mathbb{R}^M$.

The myosin concentration is mainly determined by the distribution of the muscle of Riolan and the rest of the orbicularis oculi muscle, and the lipid concentration is associated with the meibomian glands. Other relevant parameters, such as the concentration of elastin, actin, mucins, and other chromophores, could also be included in the model, and potentially could be more accurate, but on the other hand, the analysis with more parameters might be more complicated, noisier and more time-consuming. It's also preferred that the total number of parameters of all layers in the characterization vector p is smaller than the total number of spectral channels in the multispectral or hyperspectral imaging system, in order to obtain robust regression. With this trade-off in mind, the choice of the forward model is aimed to quantify meibomian glands morphology and vascular distribution in the acquired hyperspectral images with core components.

The forward mapping $p \rightarrow x$ could be analyzed with a deterministic or stochastic model. The deterministic model could be a diffusion theory model, a radiative transfer model or a Kubelka-Munk (KM) theory model, and the most common stochastic model is a Monte-Carlo model. As an example, a modified KM theory model is described herein, those skilled in the art could readily extend the analysis to other types of models.

The KM theory describes the resultant light from turbid materials with the irradiance transmittance ($t_n$) and reflectance ($r_n$) at each layer. Each layer is modeled as a homogenous layer of a material with a certain thickness that absorbs and scatters incident light. The irradiance transmittance $t_n(\lambda)$ and reflectance $r_n(\lambda)$ of the n-th layer are:

$$t_n(\lambda) = \frac{4\beta_n(\lambda)}{[1+\beta_n(\lambda)]^2 e^{K_n(\lambda)d_n} - [1-\beta_n(\lambda)]^2 e^{-K_n(\lambda)d_n}} \tag{8}$$

$$r_n(\lambda) = \frac{[1-\beta_n(\lambda)^2][e^{K_n(\lambda)d_n} - e^{-K_n(\lambda)d_n}]}{[1+\beta_n(\lambda)]^2 e^{K_n(\lambda)d_n} - [1-\beta_n(\lambda)]^2 e^{-K_n(\lambda)d_n}} \tag{9}$$

where $d_n$ is the thickness of the n-th layer, and $\beta_n(\lambda)$ and $K_n(\lambda)$ are $$\beta_n(\lambda) = \sqrt{A_n(\lambda)/[A_n(\lambda)+2S_n(\lambda)]} \tag{10}$$

$$K_n(\lambda) = \sqrt{A_n(\lambda)[A_n(\lambda)+2S_n(\lambda)]} \tag{11}$$

Further, the coefficients $A_n(\lambda)$ and $S_n(\lambda)$ are determined by the absorption coefficient $a_n(\lambda)$ and the reduced scattering coefficient $s_n'(\lambda)$ of each layer, and the final relations are dependent on the specific scattering and absorption properties of a material. In one preferred method, $$A_n(\lambda) = \frac{a_n(\lambda)}{\frac{1}{2} + \frac{1}{4}\left[1 - \frac{s_n'(\lambda)}{s_n'(\lambda)+a_n(\lambda)}\right]} \tag{12}$$

$$S_n(\lambda) = \frac{s_n'(\lambda)}{\frac{4}{3} + \frac{38}{45}\left[1 - \frac{s_n'(\lambda)}{s_n'(\lambda)+a_n(\lambda)}\right]} \tag{13}$$

Specifically, the absorption coefficient is dependent upon the chromophore types and concentrations in a layer. For example, in the top layer of an everted eyelid, the conjunctival epithelium, the absorption coefficient is modeled as $$a_1(\lambda) = p_{col\_1} a_{col}(\lambda) + p_{mel\_1} a_{mel}(\lambda) + p_{w\_1} a_w(\lambda) + p_{car\_1} a_{car}(\lambda) \tag{14}$$

where $a_{col}(\lambda)$, $a_{mel}(\lambda)$, $a_w(\lambda)$, and $a_{car}(\lambda)$ are the specific absorption coefficients of collagen, melanin, water, and β-carotene.

The absorption coefficient of the conjunctival stroma could be modeled as $$a_2(\lambda) = p_{col\_2} a_{col}(\lambda) + p_{bld\_2}[p_{o\_2} a_{ohb}(\lambda) + (1-p_{o\_2}) a_{dhb}(\lambda)] + (p_{w\_2} + 0.9 p_{bld\_2}) a_w(\lambda) + p_{car\_2} a_{car}(\lambda) + p_{bil\_2} a_{bil}(\lambda) \tag{15}$$

where $a_{ohb}(\lambda)$, $a_{dhb}(\lambda)$, and $a_{bil}(\lambda)$ are the specific absorption coefficients of oxygenated hemoglobin, deoxygenated hemoglobin, and bilirubin. It also implicitly uses the fact that water is about 90% of the blood.

As another example, the absorption coefficient of the pre-MG or post-MG tarsal plate could be modeled as a k-th layer with $$a_k(\lambda) = p_{col\_k} a_{col}(\lambda) + p_{bld\_k}[p_{o\_k} a_{ohb}(\lambda) + (1-p_{o\_k}) a_{dhb}(\lambda)] + (p_{w\_k} + 0.9 p_{bld\_k}) a_w(\lambda) + p_{car\_k} a_{car}(\lambda) + p_{bil\_k} a_{bil}(\lambda) + p_{myo\_k} a_{myo}(\lambda) \tag{16}$$

where $a_{myo}(\lambda)$ is the specific absorption coefficient of myosin, which is contained in the muscle of Riolan surrounding the meibomian glands.

Similar absorption coefficients could be derived for all the other layers with different chromophore distributions, and in general, $$a_n(\lambda) = \sum_{ch} p_{ch\_n} a_{ch}(\lambda) \tag{17}$$

where $p_{ch\_n}$ is the concentration of a type of chromophore in the n-th layer, and $a_{ch}(\lambda)$ is the specific absorption coefficient of that chromophore.

The reduced scattering coefficient of each layer is modeled with the form of $$s_n'(\lambda) = C_n \lambda^{-D_n} \tag{18}$$

where the parameters $C_n$ and $D_n$ are determined experimentally or adapted from the literature. Sometimes, $C_n$ is simplified to be linearly proportional to the collagen concentration $p_{col}$ of the n-th layer.

In the original Kubelka-Munk theory, surface reflection of the turbid material is neglected. In meibography and a lot of other applications, surface reflection has to be added into the model. At the interface of different layers, Fresnel equations could be used to model the irradiance transmittance and reflectance. In many embodiments, the distance of the eyelid to the imaging system of the meibography device is much longer than the length of a meibomian gland, hence the illumination could be approximated as normal incidence, and simplified Fresnel equations could be used. The irradiance transmittance $\tau_n(\lambda)$ and reflectance $\rho_n(\lambda)$ at the interface with normal incidence are $$\tau_n(\lambda) = \frac{4N_n(\lambda)^2}{[N_{n+1}(\lambda) + N_n(\lambda)]^2} \quad (19)$$

$$\rho_n(\lambda) = \left[\frac{N_{n+1}(\lambda) - N_n(\lambda)}{N_{n+1}(\lambda) + N_n(\lambda)}\right]^2 \quad (20)$$

where $N_n(\lambda)$ and $N_{n+1}(\lambda)$ are the refractive indices of the incident and transmitting layer.

If the incident angle is not negligible, the complete Fresnel equations could be used to derive irradiance transmittance and reflectance for oblique incidence.

Figure 11:
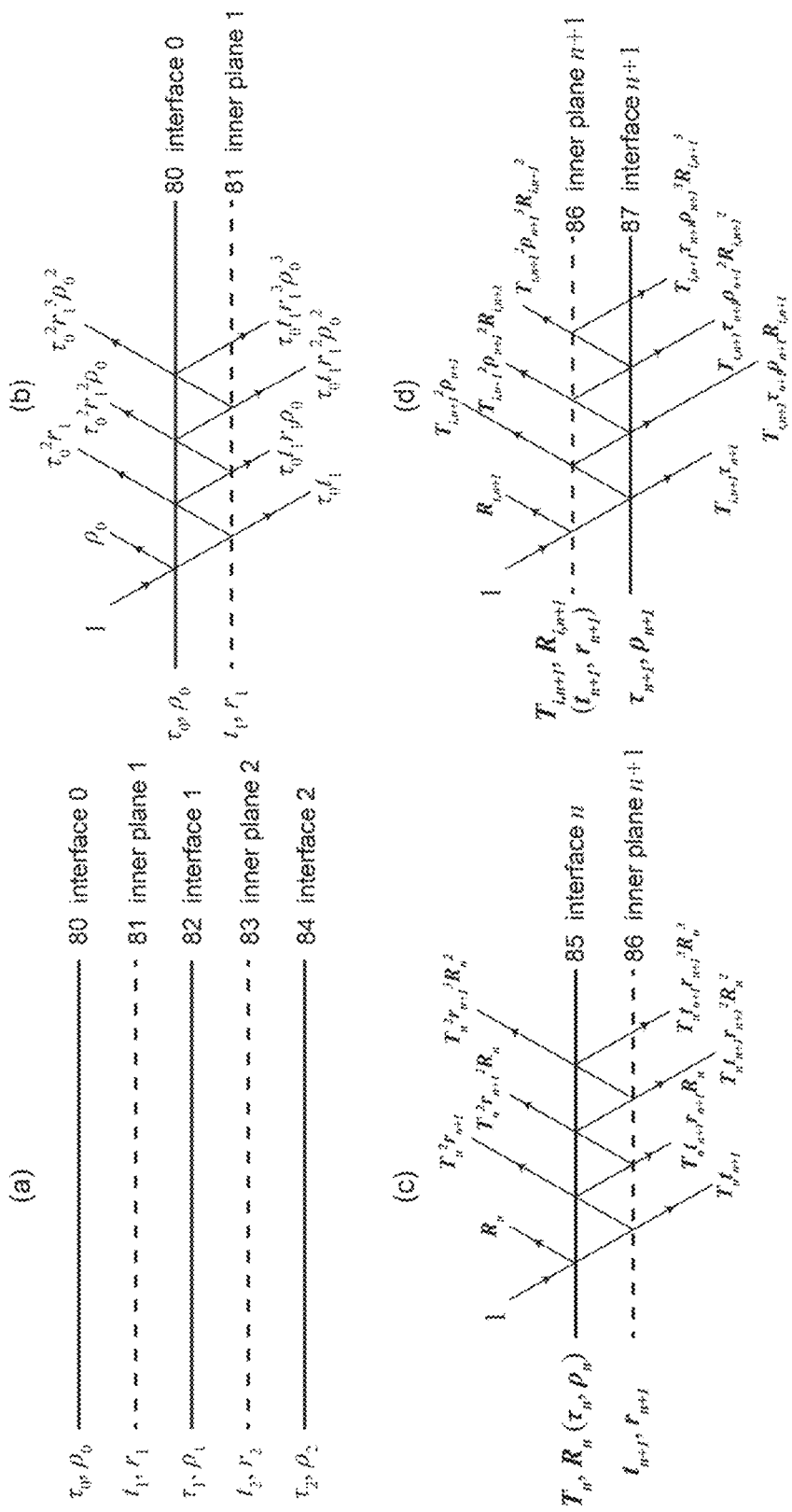
FIG. 11 presents the multiple reflection analysis in a modified Kubelka-Munk theory model of the eyelid.

In the modified KM theory model in this invention, multiple reflections between two adjacent layers and interfaces are taken into account. As shown in FIG. 11, after the calculation of the transmittance and reflectance of each layer with the KM theory, the net effect of the n-th layer could be modeled as if the transmission and reflection happen at a single plane, the n-th inner plane. Because of the material of each layer is turbid or translucent, the reflected light will add incoherently, thus the phase factors can be dropped and the exact location of the inner plane doesn't matter, as long as it's within the thickness of each layer. With this novel abstraction, each layer can be simplified as an optical plane analogous to an optical interface. In FIG. 11(a), the first several layers are plotted to represent this simplified model. Each layer is abstracted as an inner plane with two boundary interfaces. The interface 0, inner plane 1, interface 1, inner plane 2, and interface 2 are labeled as 80 to 84. The irradiance transmittance and reflectance of each interface are denoted as $\tau$ and $\rho$ for an optical interface, and as t and r for an abstracted inner plane.

In FIG. 11(b), detailed calculation of multiple reflections between the interface 0 and the inner plane 1 are plotted, and the sum of the reflectance and transmittance of these two layers are:

$$R_{i,1} = \rho_0 + \tau_0^2 r_1 \sum_{m=0}^{\infty} (r_1\rho_0)^m = \rho_0 + \frac{\tau_0^2 r_1}{1 - r_1\rho_0} \quad (21)$$

$$T_{i,1} = \tau_0 t_1 \sum_{m=0}^{\infty} (r_1\rho_0)^m = \frac{\tau_0 t_1}{1 - r_1\rho_0} \quad (22)$$

where the subscript "i" stands for an inner plane. The net effect of these two layers could be treated as a pair of new transmittance and reflectance $(T_{i,1}, R_{i,1})$ at the inner plane 1, and the next two surfaces could be analyzed. This whole calculation could be repeated in an iterative process.

FIG. 11(c) presents a general case of interface n 85, i.e. the n-th interface, and inner plane n+1 86, i.e. the (n+1)-th inner plane. The transmittance and reflectance of the interface n itself are $(\rho_n, \rho_n)$. However, taking all the layers above the n-th interface into account, the net transmittance and reflectance are $(T_n, R_n)$ at the position of the n-th interface.

The multiple reflections between the interface n and the inner plane n+1 further generate $$R_{i,n+1} = R_n + \frac{T_n^2 r_{n+1}}{1 - r_{n+1} R_n} \quad (23)$$

$$T_{i,n+1} = \frac{T_n t_{n+1}}{1 - r_{n+1} R_n} \quad (24)$$

Similarly, FIG. 11(d) illustrates the general case with an interface n+1 87, i.e. the (n+1)-th interface beneath the (n+1)-th inner plane 86. The transmittance and reflectance of the (n+1)-th inner plane itself are $(t_{n+1}, r_{n+1})$. However, taking all the layers above the (n+1)-th inner plane into account, the net transmittance and reflectance are $(T_{i,n+1}, R_{i,n+1})$ at the position of the (n+1)-th inner plane. The multiple reflections leads to $$R_{n+1} = R_{i,n+1} + \frac{T_{i,n+1}^2 \rho_{n+1}}{1 - \rho_{n+1} R_{i,n+1}} \quad (25)$$

$$T_{n+1} = \frac{T_{i,n+1} \tau_{n+1}}{1 - \rho_{n+1} R_{i,n+1}} \quad (26)$$

The above iteration in FIGS. 11(c) and (d) could be repeated until reaching the last interface or the last layer of infinite thickness in a model. The irradiance transmittance and reflectance of the entire structure are hence analyzed.

Sometimes, significant simplification of the forward model with minimal parameters is employed, if a quick and coarse evaluation of the eyelid and meibomian glands is enough. For example, the everted eyelid could be modeled as a three-layer structure of a layer of top tissue, a layer of lipids, and a layer of bottom tissue, where the middle lipid layer is of variable thickness, and the bottom tissue layer can be modeled as semi-infinite for direct illumination. Further, in one even more simplified model, the everted eyelid is modeled as a single layer with different concentration of core components, such as hemoglobin, collagen, and lipids, etc.

If the optional polarizer 23 and analyzer 24 are used in the setup, they could be of properly chosen polarization states such that the surface reflection at the superficial layer is minimized Polarization control is especially important, if a simplified eyelid model is used. For example, if the incident illumination is of horizontally polarized light, after surface reflection, the surface reflected light is mostly of horizontally polarized light. If the analyzer is a vertical analyzer, most of the surface reflected light will be blocked. As another example, if the incident illumination is of left hand circularly polarized light, the surface reflected light is mostly of right hand circularly polarized with a reversed helicity. If the analyzer is a left hand circular analyzer, most of the surface reflected light will be blocked. Light travels deeper into the tissue and scattered back after multiple scattering are of a low degree of polarization, hence part of the scattered light will be able to pass through the analyzer. Therefore, with polarization control, the surface reflection could be minimized and the deeper tissue structure, including the meibomian glands could be revealed. With polarizer 23 and analyzer 24 in place, the Fresnel equations of transmittance and reflectance, and the calculation of multiple reflections should take polarization into account, especially for oblique incidence. The depolarization of each layer related to the scattering coefficients could be estimated, and the forward model could be modified accordingly.

In the inverse model, the multispectral or hyperspectral data is used to estimate the characterization parameters of the meibomian glands and adjacent eyelid tissues:

$$x \rightarrow p \quad (27)$$

The inverse model could be parametric or non-parametric. If a parametric method of the inverse model is used, the inverse process of the forward model is used to recovery the characterization parameters. The parameter estimation based on the inverse function $f^{-1}$ of the forward model in Eq. (7) is usually difficult to obtain analytically due to the nonlinearities in the forward model. However, the parameter estimation could be obtained numerically, if the previous forward mapping function f of different combination of parameters is unique. Numerical parameter estimations are obtained after iterations starting from a guess solution with a numerical method such as Newton-Raphson method, Broyden's method, bisection method, etc. The guess solution is randomly chosen within a preset parameter range based on a priori knowledge of the eyelid tissue properties. Usually the Jacobian matrix or other similar derivative based matrices are used in the iteration process. Sometimes, an inverse model based on least-square minimization, maximum likelihood, or independent component analysis, or other methods could be used for parameter estimation of simplified eyelid models.

If non-parametric methods are used in the inverse model, the eyelid characterization parameters could be estimated with a machine learning method. The machine learning method could be supervised learning, semi-supervised learning, and unsupervised learning. In the following, a support vector machine based regression method as a representative non-parametric, supervised machine learning method for the inverse model is described.

The input training data points are $\{(x_1, p_1), (x_2, p_2), \ldots, (x_{l-1}, p_{l-1}), (x_l, p_l)\}$, where $x_i \in \mathbb{R}^M$, $p_i \in \mathbb{R}^1$, and the subscript "l" denotes the number of available training data pairs. The training data could be generated with the aforementioned forward model, or collected from experiments. The goal of the inverse model is to find a function g(x) to estimate each scalar component $p_i$ of the target vector p with a maximum deviation of $\varepsilon$:

$$g(x) = \langle w, x \rangle + b \quad (28)$$

Hence given a spectral response vector $x_i$ at a given spatial point, $g(x_i)$ is used to estimate $p_i$. However, the $\varepsilon$-precision might not be a feasible constraint sometimes, and slack variables $\xi_i$ and $\xi^*_i$ could be introduced to relax the error precision $\varepsilon$ to allow some more errors of potential outliers, with a so-called "soft margin", and the constrained optimization problem has the formulation:

$$\text{minimize } \frac{1}{2}\|w\|^2 + C\sum_{i=1}^{l}(\xi_i + \xi_i^*) \quad (29)$$

$$\text{subject to } \begin{cases} p_i - \langle w, x_i \rangle - b \leq \varepsilon + \xi_i \\ \langle w, x_i \rangle + b - p_i \leq \varepsilon + \xi_i^*, \\ \xi_i, \xi_i^* \geq 0 \end{cases}$$

where $\|w\|^2 = \langle w, w \rangle$, and the constant C determines the allowed amount of deviation of the error larger than $\varepsilon$.

The above constrained optimization problem could be simplified by solving a dual problem with Lagrange multipliers. The Lagrangian function is defined as:

$$L = \frac{1}{2}\|w\|^2 + C\sum_{i=1}^{l}(\xi_i + \xi_i^*) - \sum_{i=1}^{l}(\gamma_i \xi_i + \gamma_i^* \xi_i^*) - \sum_{i=1}^{l}\alpha_i(\varepsilon + \xi_i - p_i + \langle w, x_i \rangle + b) - \sum_{i=1}^{l}\alpha_i^*(\varepsilon + \xi_i^* + p_i - \langle w, x_i \rangle - b) \quad (30)$$

where $\gamma_i, \gamma_i^*, \alpha_i$, and $\alpha_i^*$ are Lagrange multipliers, which are assistant parameters. From the saddle point condition, the partial derivatives of the Lagrangian function have to vanish, hence $$\frac{\partial L}{\partial b} = \sum_{i=1}^{l}(\alpha_i^* - \alpha_i) = 0 \quad (31)$$

$$\frac{\partial L}{\partial w} = w - \sum_{i=1}^{l}(\alpha_i - \alpha_i^*)x_i = 0 \quad (32)$$

$$\frac{\partial L}{\partial \xi_i} = C - \alpha_i - \gamma_i = 0 \quad (33)$$

$$\frac{\partial L}{\partial \xi_i^*} = C - \alpha_i^* - \gamma_i^* = 0 \quad (34)$$

Substitute Eq. (32) into Eq. (28), the support vector expansion is obtained as $$g(x) = \sum_{i=1}^{l}(\alpha_i - \alpha_i^*)\langle x_i, x \rangle + b \quad (35)$$

The dot product $\langle x_i, x \rangle$ in Eq. (35) can be construed to be a measure of similarity. For many applications, including meibography, a nonlinear kernel function $K(x_i, x)$ can be constructed as a generalized measure of similarity, and the nonlinear support vector expansion is $$g(x) = \sum_{i=1}^{l}(\alpha_i - \alpha_i^*)K(x_i, x) + b \quad (36)$$

Common kernel functions include a polynomial kernel such as $K(x_i, x_j) = (x_i \cdot x_j + 1)^p$, a radial basis function kernel or a Gaussian kernel, such as $K(x_i, x_j) = \exp(-\|x_i - x_j\|^2/2\sigma^2)$, and a sigmoid kernel, such as $K(x_i, x_j) = \tanh(\kappa x_i \cdot x_j - \delta)$.

The constant offset parameter b could be computed with the Karush-Kuhn-Tucker (KKT) conditions, which states that the products between Lagrange multipliers and the constraints have to vanish, $$a_i(\varepsilon + \xi_i - p_i + \langle w, x \rangle + b) = 0 \quad (37)$$

$$a^*_i(\varepsilon + \xi^*_i + p_i - \langle w, x \rangle - b) = 0 \quad (38)$$

$$(C - a_i)\xi_i = 0 \quad (39)$$

$$(C - a^*_i)\xi^*_i = 0 \quad (40)$$

Together with the analysis of the Lagrange multipliers, b could be computed.

In the support vector regression analysis, each parameter of the input eyelid characterization vector $p = [p_{th0}, p_{th1}, p_{th2}, p_{col}, p_{mel}, p_{car}, p_{bil}, p_{myo}, p_{lip}, p_w, p_{bld}, p_o]$ is estimated independently with Eq. (36). Repeat the regression process for all the characterization parameters, and the parameter estimation of the entire eyelid could be obtained in the inverse model.

Similar process of the inverse model could be done with other machine learning methods, such as artificial neural networks, k-nearest neighbors algorithm, etc.

Note that the above forward model and inverse model are for an everted eyelid from the conjunctival side. However, similar procedures could be applied to an eyelid from the anterior skin side (cutaneous side) as well.

Further, the multispectral and hyperspectral devices could also focus at the eyelid margin, instead of the inner eyelid surface, as shown in FIG. 9. The meibomian gland orifices of MGD patients could develop inspissated lipids clogging, capping, pouting, retroplacement, obliteration, and there could be hyperkeratinization of the eyelid margin, and potential crusting at the base of the eyelashes due to blepharitis. Multispectral and hyperspectral meibography could be used to image meibomian gland distribution, meibomian gland orifices and eyelashes to investigate all of these pathological features.

Figure 12:
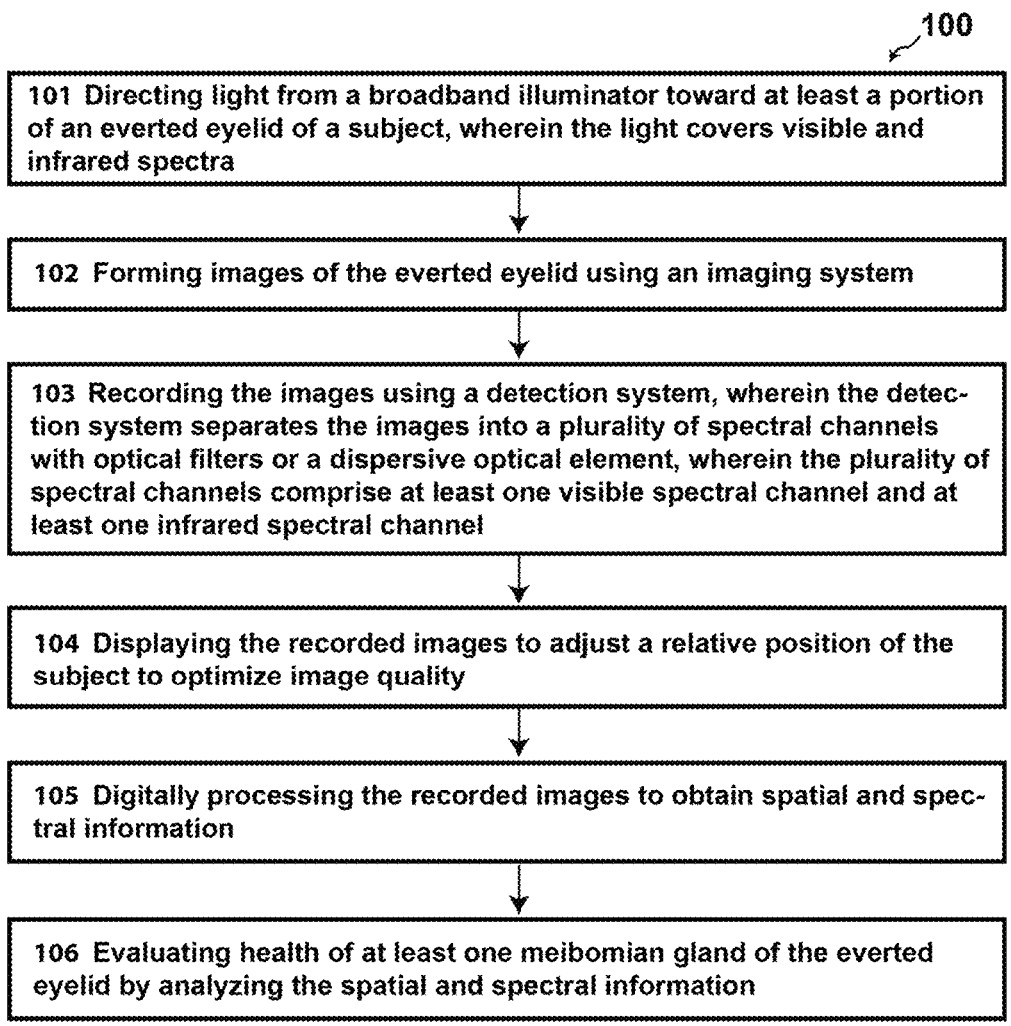
FIG. 12 presents a flowchart of the method of multispectral and hyperspectral meibography.
Figure 13:
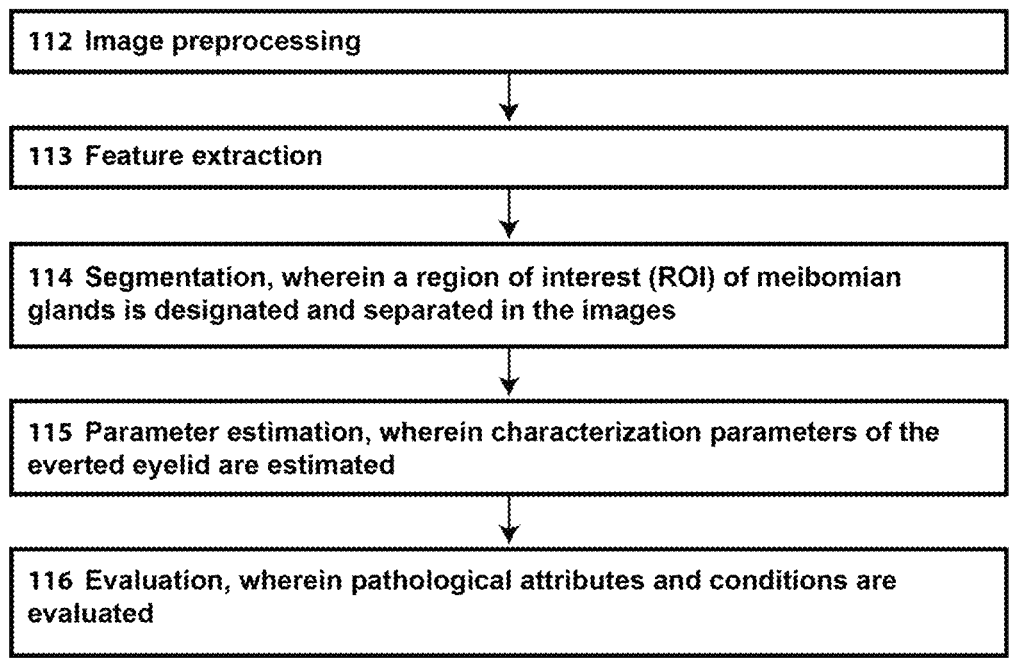
FIG. 13 presents a flowchart of the digital processing steps of multispectral and hyperspectral meibography.

FIG. 12 presents a flowchart representing method 100 of the disclosed multispectral and hyperspectral meibography. Method 100 includes (101) directing light from a broadband illuminator toward at least a portion of an everted eyelid of a subject, wherein the light covers visible and infrared spectra; (102) forming images of the everted eyelid using an imaging system; (103) recording the images using a detection system, wherein the detection system separates the images into a plurality of spectral channels with optical filters or a dispersive optical element, wherein the plurality of spectral channels comprise at least one visible spectral channel and at least one infrared spectral channel; (104) displaying the recorded images to adjust a relative position of the subject to optimize image quality; (105) digitally processing the recorded images to obtain spatial and spectral information; (106) evaluating health of at least one meibomian gland of the everted eyelid by analyzing the spatial and spectral information. In some embodiments, Method 100 further comprises (107) controlling the broadband illuminator, the imaging system, and the detection system with a control system.

In a preferred embodiment, the step of digital processing 105 comprises (112) image preprocessing, which includes reflectance calibration, transmittance calibration, image smoothing, contrast enhancement, and removal of illumination nonuniformity; (113) feature extraction, wherein the original data dimensionality is reduced and the most important subset of the original data is obtained to extract relevant feature information of the everted eyelid; (114) segmentation, wherein a region of interest (ROI) of meibomian glands is designated and separated in the images; (115) parameter estimation, wherein characterization parameters of the everted eyelid are estimated; (116) evaluation, wherein pathological attributes and conditions are evaluated, including a percentage of meibomian gland coverage within the ROI, the meibomian gland atrophy, meibomian gland thickness and tortuosity.

In the following, three embodiments are disclosed. Embodiment 1 and 2 are stationary multispectral and hyperspectral meibography devices for clinical use. Embodiment 3 is a portable, handheld multispectral meibography device.

Embodiment 1

Figure 14:
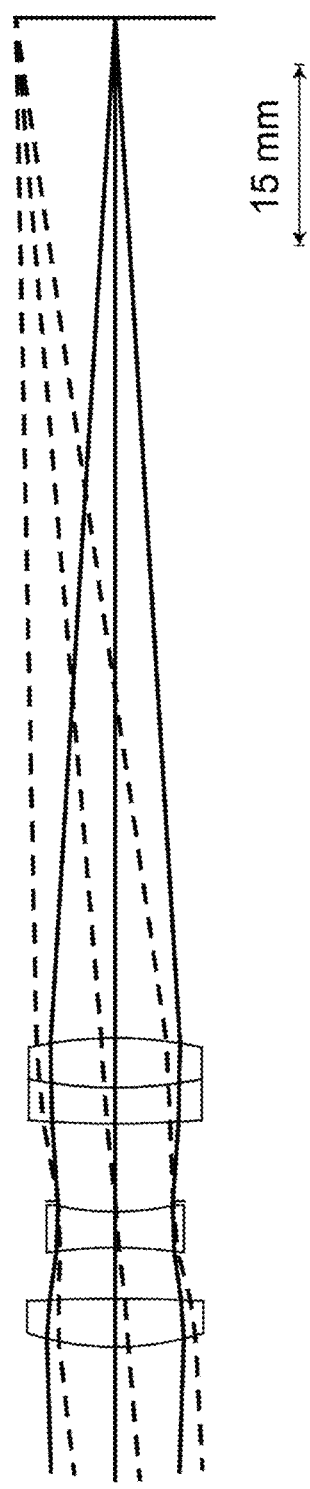
FIG. 14 presents one embodiment of the imaging system and the detection system of multispectral and hyperspectral meibography.

FIG. 14 presents one preferred embodiment, Embodiment 1, of the imaging system and the detection system of the multispectral and hyperspectral meibography device. It is optimized in the spectral range of visible and infrared spectra up to 950 nm for a sensor with a diagonal length of 16.4 mm. The image F/#=8, and the system magnification=−0.5×.

The numerical details of Embodiment 1 are listed in Table 1, and the length values are in units of mm.

TABLE 1

| Surface Number | Radius of curvature | Thickness | $n_d$ | $V_d$ | Semi-Aperture |
|---|---|---|---|---|---|
| Object | Infinity | 180 | | | |
| 1 | 23.5268 | 4 | 1.607381 | 56.6501 | 6.61 |
| 2 | −164.8068 | 4.2613 | | | 6.19 |
| 3 | −38.5523 | 3 | 1.620053 | 36.4309 | 5.15 |
| 4 | 23.0985 | 0.8712 | | | 4.76 |
| 5-Stop | Infinity | 6.4642 | | | 4.75 |
| 6 | 89.6388 | 3 | 1.620053 | 36.4309 | 5.95 |
| 7 | 36.3950 | 4.1194 | 1.607381 | 56.6501 | 6.24 |
| 8 | −33.2881 | 84.9892 | | | 6.49 |
| 9-Image | Infinity | | | | 8.20 |

The object distance is 180 mm, and the overall length of Embodiment 1 from Surface 1 to the image plane is 110.71 mm. From the object side to the image side, Surfaces 1 to 2 is a positive lens, forming the first positive group 12 in FIG. 1. Surfaces 3 to 4 is a negative lens, forming the negative group 13 in FIG. 1. Surface 5 is the aperture stop. Surfaces 6 to 8 is a positive doublet, forming the second positive group 14 in FIG. 1. Further, the back focal length from Surface 8 to the image plane Surface 9 is 84.99 mm, which is large enough to insert a dichroic beamsplitter, an acousto-optic tunable filter or liquid crystal tunable filter, if preferred. If optical filters are inserted, the design parameters could be readily adjusted to optimize the image quality.

Embodiment 2

Figure 15:
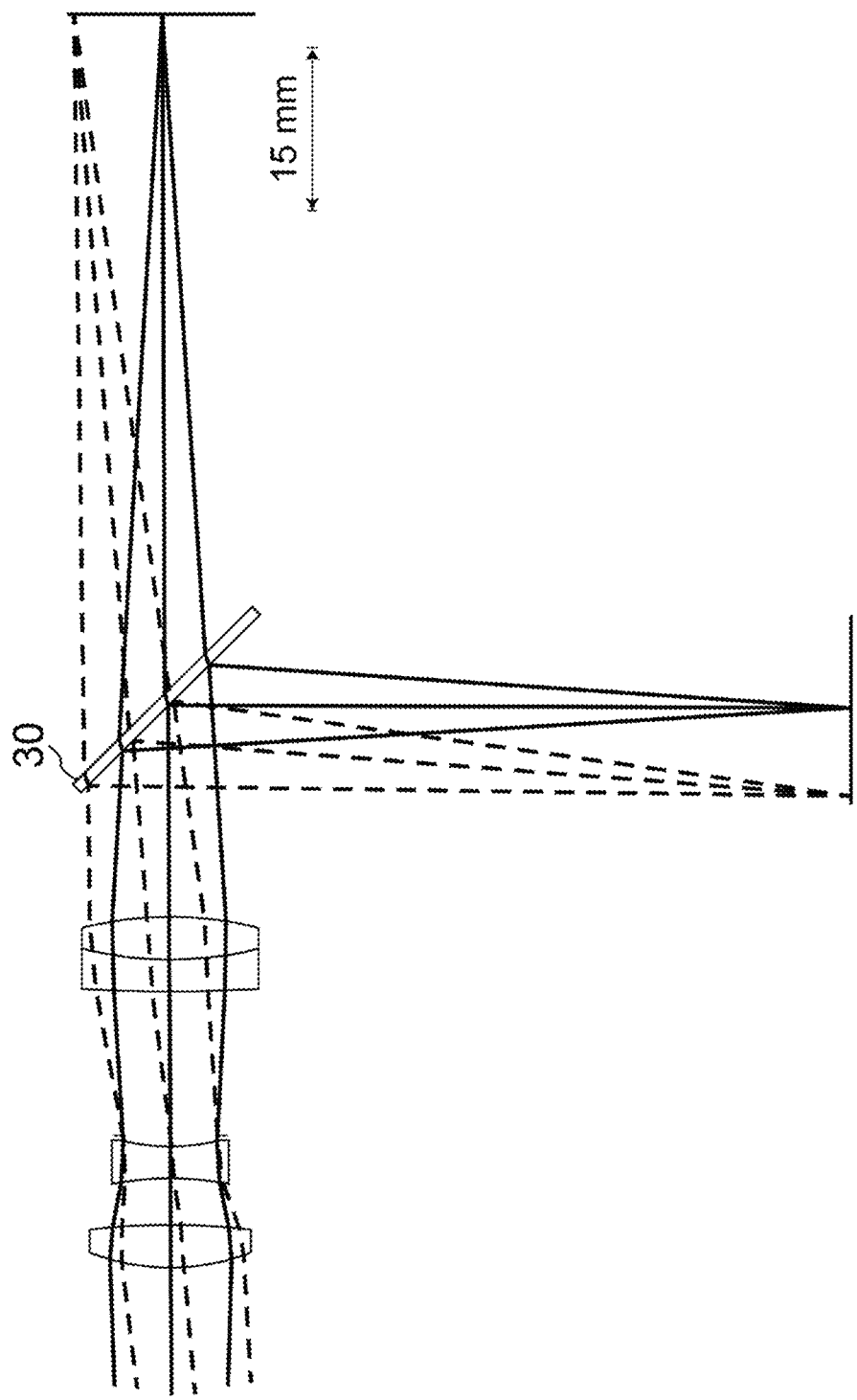
FIG. 15 presents another embodiment of the imaging system and the detection system of multispectral and hyperspectral meibography using a dichroic beamsplitter.

FIG. 15 presents another preferred embodiment, Embodiment 2, of the imaging system and the detection system of the multispectral and hyperspectral meibography device. Embodiment 2 uses a dichroic beamsplitter 30 as previously shown in FIG. 3(c). It is optimized in the spectral range of visible and infrared spectra up to 950 nm for a sensor with a diagonal length of 16.4 mm The image F/#=8, and the system magnification=−0.5×.

The numerical details of Embodiment 2 are listed in Table 2, and the length values are in units of mm.

TABLE 2

| Surface Number | Radius of curvature | Thickness | $n_d$ | $V_d$ | Semi-Aperture |
|---|---|---|---|---|---|
| Object | Infinity | 180 | | | |
| 1 | 20.5080 | 4 | 1.607381 | 56.6501 | 6.82 |
| 2 | −64.4761 | 4.3710 | | | 6.40 |
| 3 | −27.7782 | 3 | 1.620053 | 36.4309 | 4.93 |
| 4 | 19.1004 | 1 | | | 4.42 |
| 5-Stop | Infinity | 13.5287 | | | 4.39 |
| 6 | 135.8552 | 3 | 1.620053 | 36.4309 | 6.90 |
| 7 | 33.7857 | 4 | 1.607381 | 56.6501 | 7.23 |
| 8 | −33.2442 | 20 | | | 7.45 |
| 9 | Infinity | 1.05 | 1.458467 | 67.7963 | 10.80 |
| 10 | Infinity | 63.9590 | | | 7.33 |
| 11-Image | Infinity | | | | 8.20 |

The object distance is 180 mm, and the overall length of Embodiment 2 from Surface 1 to the image plane is 117.91 mm. From the object side to the image side, Surfaces 1 to 2 is a positive lens, forming the first positive group 12 in FIG. 1. Surfaces 3 to 4 is a negative lens, forming the negative group 13 in FIG. 1. Surface 5 is the aperture stop. Surfaces 6 to 8 is a positive doublet, forming the second positive group 14 in FIG. 1. Surfaces 9 to 10 is a dichroic beamsplitter 30. Further, the back focal length from Surface 10 to the image plane Surface 11 is 63.96 mm.

Embodiment 1 and 2 are mainly used for multispectral meibography. However, if the illumination system includes a tunable spectral filter to adjust the illumination wavelength in use, or a spectrometer system is used in the detection system, Embodiment 1 and 2 could also be used for hyperspectral meibography.

Figure 16:
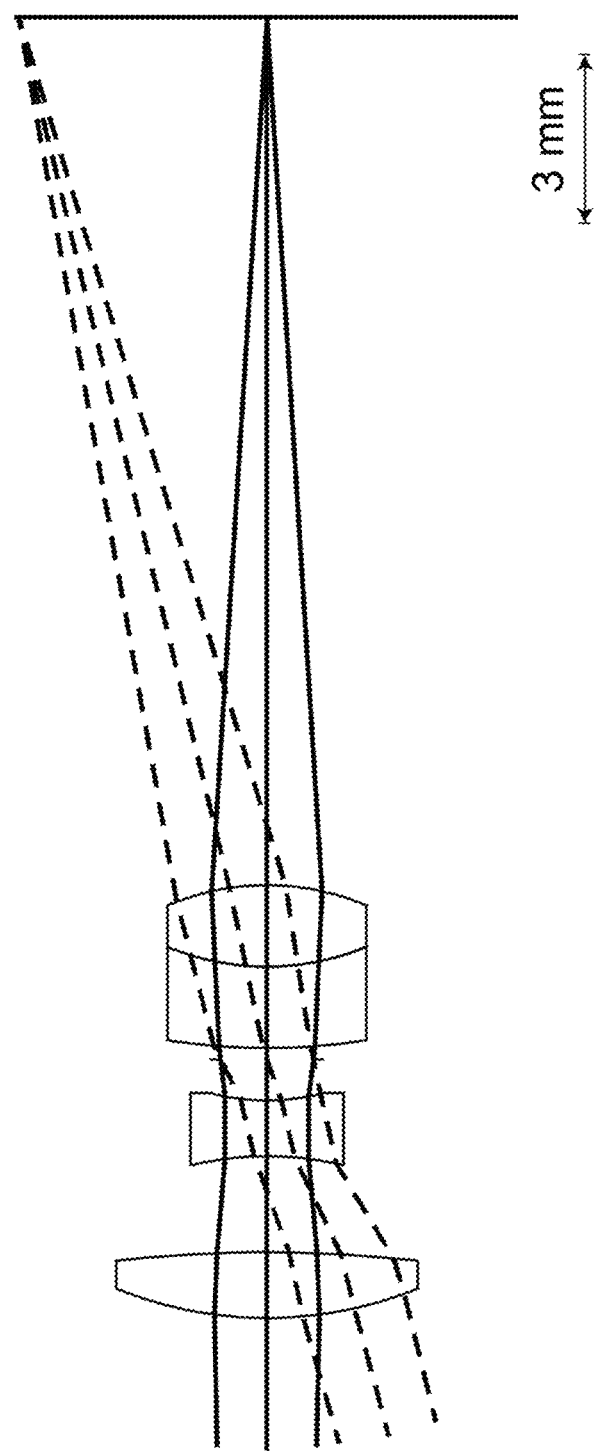
FIG. 16 presents one embodiment of the imaging system and the detection system of a handheld multispectral meibographer.

This invention also discloses a handheld multispectral meibography device, as shown in FIG. 16, to conveniently inspect the meibomian gland morphology and the eyelid margin health. A portable, handheld diagnostic device with a compact design has the advantages of flexible use in different environments, fast imaging and quick diagnostic feedback.

Embodiment 3

FIG. 16 presents one preferred embodiment, Embodiment 3, of the imaging system and the detection system of a handheld multispectral meibography device. It is optimized in the spectral range of visible and infrared spectra up to 1050 nm for a sensor with a diagonal length of 9 mm. The image F/#=8, and the system magnification=−0.3×.

The numerical details of Embodiment 3 are listed in Table 3, and the length values are in units of mm.

TABLE 3

| Surface Number | Radius of curvature | Thickness | $n_d$ | $V_d$ | Semi-Aperture |
|---|---|---|---|---|---|
| Object | Infinity | 50 | | | |
| 1 | 7.1833 | 1.2006 | 1.607381 | 56.6501 | 2.48 |
| 2 | −24.1589 | 1.7601 | | | 2.29 |
| 3 | −5.7314 | 1.0186 | 1.620053 | 36.4309 | 1.26 |
| 4 | 3.9449 | 0.7488 | | | 0.97 |
| 5-Stop | Infinity | 0.2086 | | | 0.84 |
| 6 | 11.3778 | 1.4998 | 1.620053 | 36.4309 | 0.97 |
| 7 | 4.6125 | 1.4920 | 1.607381 | 56.6501 | 1.38 |
| 8 | −4.5004 | 15.8765 | | | 1.63 |
| 9-Image | Infinity | | | | 4.50 |

The object distance is 50 mm, and the overall length of Embodiment 3 from Surface 1 to the image plane is 23.81 mm. This compact design is suitable for handheld requirement. From the object side to the image side, Surfaces 1 to 2 is a positive lens, forming the first positive group 12 in FIG. 1. Surfaces 3 to 4 is a negative lens, forming the negative group 13 in FIG. 1. Surface 5 is the aperture stop. Surfaces 6 to 8 is a positive doublet, forming the second positive group 14 in FIG. 1. Further, the back focal length from Surface 8 to the image plane Surface 9 is 15.88 mm, which is large enough to insert a dichroic beamsplitter or other optical filters, if preferred.

Figure 17:
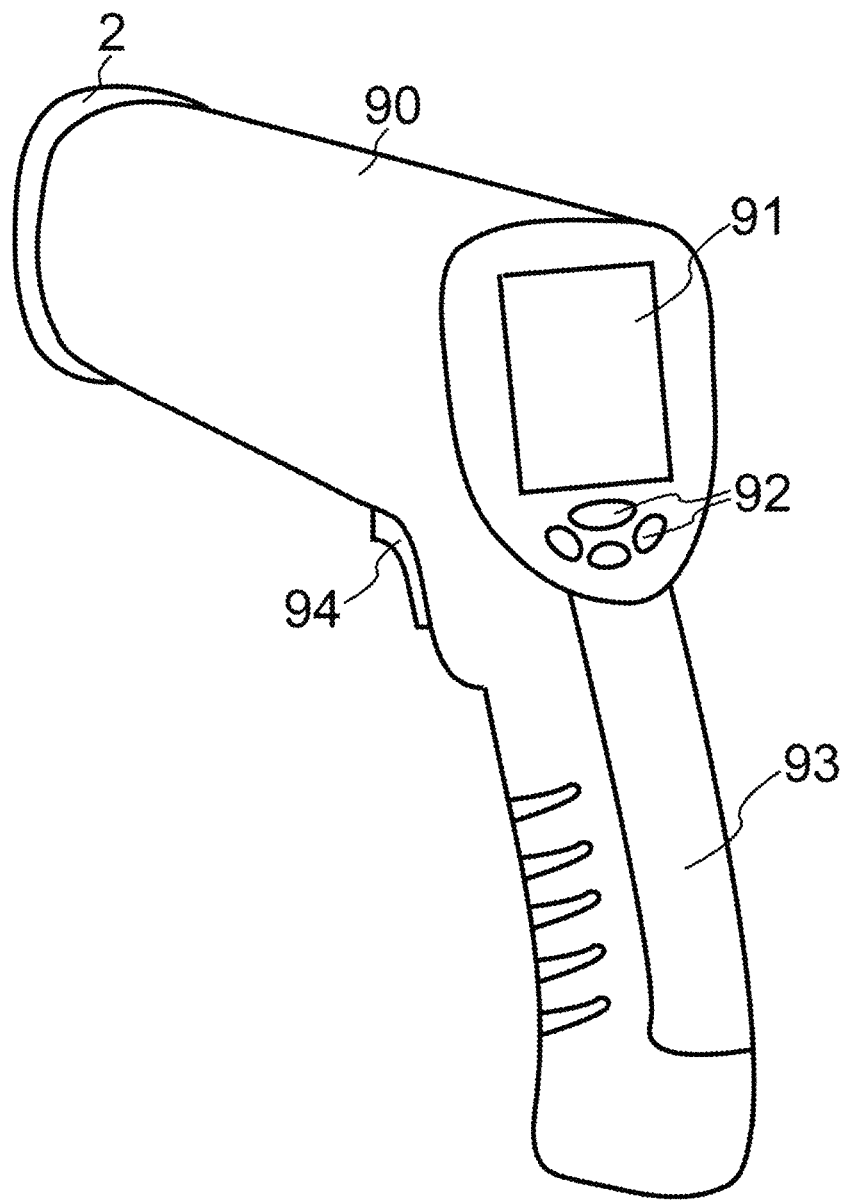
FIG. 17 presents one embodiment of the exterior of a handheld meibographer.

FIG. 17 presents one embodiment of the exterior of a handheld meibographer. An illuminator 2 is connected to an exterior package 90. The imaging system and the detection system are inside of 90. An optional polarizer 23 (not shown in FIG. 17) could be placed in the anterior part of 2. A liquid-crystal display (LCD) screen 91 is used to display real time images to adjust the relative position of the meibographer and the patient to obtain sharp images of an everted eyelid. Screen control buttons 92 are used to control the LCD. A handle 93 is to be held by the operator. A record trigger 94 could be pressed, when a sharp image of the eyelid is in focus.

The invention has been described in detail with particular reference to certain preferred embodiments thereof, but it will be understood that variations and modifications can be effected within the spirit and scope of the invention.

All publications, patents and patent applications referred to herein are incorporated by reference in their entirety to the same extent as if each individual publication, patent or patent application was specifically and individually indicated to be incorporated by reference in its entirety in the present application.

What is claimed is:

1. A method performed by a multispectral or hyperspectral meibomian gland imaging device, the method comprising:
    directing light from a broadband illuminator toward at least a portion of an everted eyelid of a subject, wherein said light covers visible and infrared spectra;
    forming images of said everted eyelid using an imaging system wherein said imaging system comprises a plurality of lens groups;
    recording said images using a detection system, wherein said detection system separates said images into a plurality of spectral channels with optical filters or a dispersive optical element, wherein said a plurality of spectral channels comprise at least one visible spectral channel and at least one infrared spectral channel;
    displaying said recorded images to adjust a relative position of said subject to optimize image quality;
    digitally processing said recorded images to obtain spatial and spectral information;
    evaluating health of at least one meibomian gland of said everted eyelid by analyzing said spatial and spectral information.

2. The method of claim 1, further comprising:
    controlling said broadband illuminator, said imaging system, and said detection system with a control system.

3. The method of claim 1, wherein said illuminator comprises a polarizer with at least one polarization state.

4. The method of claim 1, wherein an analyzer is placed in either said imaging system or said detection system, wherein said analyzer comprises at least one polarization state.

5. The method of claim 4, wherein said illuminator comprises a polarizer with at least one polarization state, wherein at least one pair of polarization states of said polarizer and said analyzer are chosen to minimize superficial surface reflection of said everted eyelid.

6. The method of claim 1, wherein said illuminator directs light toward said everted eyelid with direct illumination without contacting said everted eyelid, wherein reflected and back scattered light from said everted eyelid is collected into said imaging system.

7. The method of claim 1, wherein said illuminator is placed behind a cutaneous side of said everted eyelid with transillumination, wherein transmitted and forward scattered light through said everted eyelid is collected into said imaging system.

8. The method of claim 1, wherein said illuminator comprises a tunable narrow band filter or a dispersive optical element to adjust the illumination spectrum.

9. The method of claim 1, wherein said detection system is a spectrometer system.

10. The method of claim 9, wherein said spectrometer system comprises a member selected from a group consisting of a transmissive spectrometer, a Czerny-Turner spectrometer, a Littrow spectrometer, an Ebert-Fastie spectrometer, an Eagle spectrometer, a Wadsworth spectrometer, a Dyson spectrometer, and a Fourier transform spectrometer.

11. The method of claim 1, wherein said optical filters are narrow band spectral filters or dichroic beamsplitters.

12. The method of claim 1, wherein said dispersive optical element is a member selected from a group consisting of a transmission grating, a reflective diffraction grating, a holographic grating, a prism, and a diffractive lens.

13. The method of claim 1, wherein said digital processing comprises:
    image preprocessing;
    feature extraction;
    segmentation, wherein a region of interest of meibomian glands is designated and separated in said images;
    parameter estimation, wherein characterization parameters of said everted eyelid are estimated;
    evaluation, wherein pathological attributes and conditions are evaluated based on said characterization parameters.

14. The method of claim 13, wherein said image preprocessing comprises reflectance calibration, transmittance calibration, image smoothing, contrast enhancement, and removal of illumination nonuniformity.

15. The method of claim 13, wherein said feature extraction comprises: generating additional digital spectral channels, by combination of at least two of said plurality of spectral channels of said detection system; generating false color images of said everted eyelid by selecting and combining spectral channels out of said plurality of spectral channels of said detection system and said additional digital spectral channels.

16. The method of claim 13, wherein said parameter estimation comprises a multilayer model of said everted eyelid, wherein each layer is modeled by said characterization parameters, wherein an inverse model based on a parametric method or a machine learning method is used for said parameter estimation.

17. The method of claim 16, wherein said machine learning method comprises a member selected from a group consisting of support vector machines, artificial neural networks, k-nearest neighbors algorithm.

18. The method of claim 1, wherein evaluating health comprises assessing an interconnection of palpebral vasculature and said at least one meibomian gland by image fusion with said at least one visible spectral channel and said at least one infrared spectral channel.

19. The method of claim 1, wherein evaluating health comprises evaluating meibomian gland orifice obstruction and palpebral vasculature of the everted eyelid with images of an eyelid margin.

* * * * *